US010315975B2

(12) United States Patent
Strautmann et al.

(10) Patent No.: US 10,315,975 B2
(45) Date of Patent: Jun. 11, 2019

(54) METHOD FOR THE HYDROFORMYLATION OF 2-SUBSTITUTED BUTADIENES AND THE PRODUCTION OF SECONDARY PRODUCTS THEREOF, ESPECIALLY AMBROX

(71) Applicants: BASF SE, Ludwigshafen (DE); Ruprecht-Karls-Universität Heidelberg, Heidelberg (DE); Christa Johanna Hofmann; Stefanie Hoffman, Ludwigshafen (DE)

(72) Inventors: Julia Strautmann, Erlangen (DE); Stefan Rüdenauer, Weinheim (DE); Christian Rein, Heddesheim (DE); Melanie Weingarten, Ratzeburg (DE); Rocco Paciello, Bad Dürkheim (DE); Wolfgang Siegel, Limburgerhof (DE); Michael Breuer, Darmstadt (DE); Peter Hofmann, Heidelberg (DE); Sebastian Schmidt, Langenfeld (DE)

(73) Assignees: BASF SE, Ludwigshafen (DE); Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 15/743,153

(22) PCT Filed: Jul. 8, 2016

(86) PCT No.: PCT/EP2016/066225
§ 371 (c)(1),
(2) Date: Jan. 9, 2018

(87) PCT Pub. No.: WO2017/009205
PCT Pub. Date: Jan. 19, 2017

(65) Prior Publication Data
US 2018/0273458 A1 Sep. 27, 2018

(30) Foreign Application Priority Data
Jul. 10, 2015 (EP) .................................... 15176280

(51) Int. Cl.
*C07C 45/50* (2006.01)
*B01J 31/00* (2006.01)
*C07C 47/21* (2006.01)
*C07D 307/92* (2006.01)
*C07C 29/141* (2006.01)
*C07C 29/56* (2006.01)
*B01J 31/18* (2006.01)
*C07C 33/025* (2006.01)

(52) U.S. Cl.
CPC ............. *C07C 45/50* (2013.01); *B01J 31/186* (2013.01); *B01J 31/1865* (2013.01); *C07C 29/141* (2013.01); *C07C 29/56* (2013.01); *C07C 33/025* (2013.01); *C07C 47/21* (2013.01); *C07D 307/92* (2013.01); *B01J 2231/321* (2013.01); *C07C 2531/18* (2013.01)

(58) Field of Classification Search
CPC ........ C07C 45/50; C07C 27/21; B01L 31/186
See application file for complete search history.

(56) References Cited

U.S. PATENT DOCUMENTS

| | | |
|---|---|---|
| 4,778,929 A | 10/1988 | Zehner et al. |
| 5,728,893 A | 3/1998 | Becker et al. |
| 6,642,420 B1 | 11/2003 | Zehner et al. |
| 6,881,867 B2 | 4/2005 | Ahlers et al. |
| 6,977,312 B2 | 12/2005 | Ahlers et al. |
| 7,015,361 B2 | 3/2006 | Zehner et al. |
| 7,145,042 B2 | 12/2006 | Volland et al. |
| 7,173,138 B2 | 2/2007 | Ahlers et al. |
| 8,759,043 B2 | 6/2014 | Breuer et al. |
| 2004/0110960 A1 | 6/2004 | Ahlers et al. |
| 2006/0224000 A1 | 10/2006 | Papp et al. |
| 2010/0099875 A1 | 4/2010 | Stephan et al. |
| 2010/0105958 A1* | 4/2010 | Scheibel ............... C07C 29/141 568/494 |
| 2013/0273619 A1 | 10/2013 | Bonnekessel et al. |
| 2016/0168597 A1 | 6/2016 | Breuer et al. |
| 2016/0176803 A1 | 6/2016 | Weingarten et al. |
| 2016/0194272 A1 | 7/2016 | Weingarten et al. |
| 2016/0194273 A1 | 7/2016 | Weingarten et al. |
| 2016/0201093 A1 | 7/2016 | Breuer et al. |
| 2016/0304415 A1 | 10/2016 | Schwartztrauber et al. |
| 2016/0332944 A1 | 11/2016 | Rudenauer et al. |
| 2017/0037020 A1 | 2/2017 | Rudenauer et al. |
| 2017/0037022 A1 | 2/2017 | Stork et al. |
| 2017/0044084 A1 | 2/2017 | Schelwies et al. |
| 2017/0066705 A1 | 3/2017 | Hickmann |
| 2017/0145451 A1 | 5/2017 | Baldenius et al. |
| 2017/0175267 A1 | 6/2017 | Strautmann et al. |
| 2017/0217884 A1 | 8/2017 | Schäfer et al. |
| 2017/0233338 A1 | 8/2017 | Schäfer et al. |

(Continued)

FOREIGN PATENT DOCUMENTS

| | | |
|---|---|---|
| DE | 10342760 A1 | 3/2004 |
| EP | 423769 A2 | 4/1991 |
| EP | 1114017 A1 | 7/2001 |
| EP | 1231198 A1 | 8/2002 |
| EP | 1283843 A1 | 2/2003 |

(Continued)

OTHER PUBLICATIONS

U.S. Appl. No. 15/136,112, Hoffmann et al.
(Continued)

*Primary Examiner* — Sikarl A Witherspoon
(74) *Attorney, Agent, or Firm* — Drinker Biddle & Reath LLP

(57) ABSTRACT

The present invention relates to a method for the regioselective hydroformylation of polyunsaturated acyclic hydrocarbons, which are 1, 3 butadienes, which, in the 2 position, bear a saturated or monounsaturated or polyunsaturated acyclic hydrocarbon radical. The present invention also relates to the production of secondary products of these hydroformylation products, especially of ambrox.

17 Claims, No Drawings

(56) References Cited

U.S. PATENT DOCUMENTS

| | | |
|---|---|---|
| 2017/0233780 A1 | 8/2017 | Breuer et al. |
| 2017/0233865 A1 | 8/2017 | Strautmann et al. |
| 2017/0275225 A1 | 9/2017 | Riedel et al. |
| 2017/0283352 A1 | 10/2017 | Fenlon et al. |
| 2017/0292084 A1 | 10/2017 | Stork et al. |
| 2017/0305849 A1 | 10/2017 | Schafer et al. |
| 2017/0305850 A1 | 10/2017 | Schafer et al. |
| 2017/0355670 A1 | 12/2017 | Rudenauer et al. |
| 2018/0002266 A1 | 1/2018 | Bru Roig et al. |
| 2018/0010208 A1 | 1/2018 | Urch et al. |

FOREIGN PATENT DOCUMENTS

| | | |
|---|---|---|
| FR | 2887253 A1 | 12/2006 |
| WO | WO-9206063 A2 | 4/1992 |
| WO | WO-9950214 A1 | 10/1999 |
| WO | WO-0009467 A1 | 2/2000 |
| WO | WO-0158589 A1 | 8/2001 |
| WO | WO-0187901 A1 | 11/2001 |
| WO | WO-0222261 A2 | 3/2002 |
| WO | WO-02083695 A1 | 10/2002 |
| WO | WO-03018192 A2 | 3/2003 |
| WO | WO-2004026803 A1 | 4/2004 |
| WO | WO-2005009934 A2 | 2/2005 |
| WO | WO-2005039762 A1 | 5/2005 |
| WO | WO-2005063730 A1 | 7/2005 |
| WO | WO-2010033976 A2 | 3/2010 |
| WO | WO-2010139719 A2 | 12/2010 |
| WO | WO-2013156398 A1 | 10/2013 |
| WO | WO-2014114615 A1 | 7/2014 |

OTHER PUBLICATIONS

U.S. Appl. No. 15/509,993, Navickas et al.
U.S. Appl. No. 15/510,268, Puhl et al.
U.S. Appl. No. 15/536,524, Schelwies et al.
U.S. Appl. No. 15/555,723, Klos et al.
U.S. Appl. No. 15/559,962, Navickas et al.
U.S. Appl. No. 15/571,274, Germain et al.
U.S. Appl. No. 15/573,276, Huguet et al.
U.S. Appl. No. 15/575,169, Bru Roig et al.
U.S. Appl. No. 15/577,570, Swaminathan et al.
U.S. Appl. No. 15/577,590, Schein-Albrecht et al.
U.S. Appl. No. 15/578,959, Bri Riog et al.
Barrero, A., et al., "Synthesis of (±)-Ambrox from (E)-Nerolidol and b-Ionone via Allylic Alcohol [2,3] Sigmatropic Rearrangement", Journal of Organic Chemistry, vol. 61, No. 6, (1996), pp. 2215-2218.
Barros, H., et al., "Hydroformylation of Monoterpenic Polyenes: Effect of the Conjugation of Double Bonds on Reactivity", Organometallics, vol. 27, No. 17, (2008), pp. 4523-4531.
Barros, H., et al., "Rhodium-Catalyzed Hydroformylation of Isoprene: Unusual Accelerating Effects of Phosphorus Ligands and Gas Pressure", Organometallics, vol. 26, No. 9, (2007), pp. 2211-2218.
Foca, C., et al., "Hydroformylation of myrcene: metal and ligand effects in the hyroformylation of conjugated dienes", New Journal of Chemistry, vol. 27, (2003), pp. 533-539.
International Search Report for PCT/EP2016/066225 dated Sep. 14, 2016.
International Preliminary Report on Patentability with Written Opinion for International Application No. PCT/EP2016/066225, dated Jan. 16, 2018.
Ishimara, K., et al., "Enantio- and Diastereoselective Stepwise Cyclization of Polyprenoids Induced by Chiral and Achiral LBAs. A New Entry to (-31 )-Ambrox, (+)-Podocarpa-8,11,13-triene Diterpenoids, and (-31 )-Tetracyclic Polyprenoid of Sedimentary Origin", Journal of the American Chemical Society, vol. 124, No. 14, (2002), pp. 3647-3655.
Vlad, P., et al., "Superacid Cyclization of Homo- and Bishomoisoprenoid Acids", translated to English from Khimiya Geterotsiklicheskikh Soedinenii, No. 3, Plenum Publishing Corporation, 1991, pp. 246-249.
Written Opinion of the International Searching Authority for PCT/EP2016/066225 dated Sep. 14, 2016.

* cited by examiner

METHOD FOR THE HYDROFORMYLATION OF 2-SUBSTITUTED BUTADIENES AND THE PRODUCTION OF SECONDARY PRODUCTS THEREOF, ESPECIALLY AMBROX

CROSS-REFERENCE TO RELATED APPLICATIONS

This application is a national stage application (under 35 U.S.C. § 371) of PCT/EP2016/066225, filed Jul. 8, 2016, which claims benefit of European Application No. 15176280.4, filed Jul. 10, 2015, both of which are incorporated herein by reference in their entirety.

BACKGROUND OF THE INVENTION

The present invention relates to a process for the regioselective hydroformylation of polyunsaturated acyclic hydrocarbons, which are 1,3-butadienes which carry in the 2-position a saturated or mono- or polyunsaturated acyclic hydrocarbon radical. The present invention further relates to the preparation of secondary products of these hydroformylation products and specifically of ambrox.

PRIOR ART

The hydroformylation of butadiene compounds of the general formula A

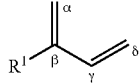
(A)

which carry in the beta-position (or 2-position) an alkyl radical, or a mono- or polyunsaturated alkenyl radical, for example isoprene or myrcene, leads to an isomer mixture using the known rhodium catalysts. Hereinbelow, to aid understanding when designating the substituent positions both of the starting materials and of the hydroformylation products, the naming depicted above in the butadiene starting compound (A) is retained.

The main product is formed in most of the syntheses known in the literature as a result of hydroformylation in the alpha-position, with simultaneous isomerization of the double bond. In the case of isoprene (B1), the main product is therefore mostly 3-methyl-pentenal (B2) and in the case of ß-myrcene (=7-methyl-3-methylene-1,6-octadiene) (C1) 3-ethylidene-7-methyl-oct-6-enal (C2):

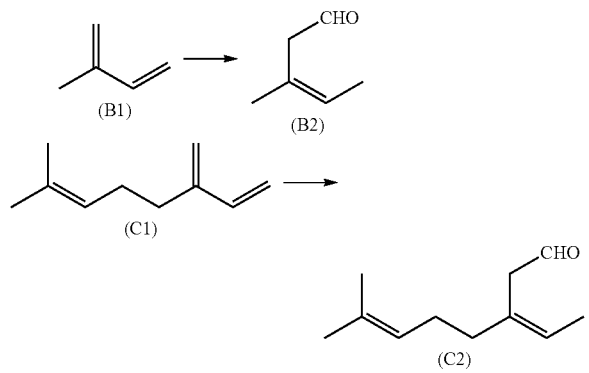

For various applications, for example for the synthesis of aroma chemicals (fragrances and flavors), it is desired that the hydroformylation proceeds with a different regioselectivity to that in accordance with the processes known hitherto, the aim being to achieve as high a yield as possible of the hydroformylation products in the delta-position. The desired main product for example during the hydroformylation of isoprene (B1) would then be 4-methylpent-4-enal (B3)

(B3)

and the desired main product during the hydroformylation of myrcene (C1) would then be 8-methyl-4-methylene-non-7-enal (C3):

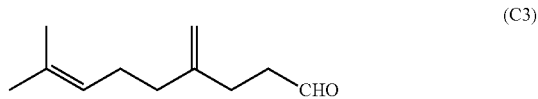
(C3)

A further interesting substrate for the regioselective hydroformylation in the delta-position is trans-ß-farnesene ((6E)-7,11-dimethyl-3-methylene-1,6,10-dodecatriene) (D):

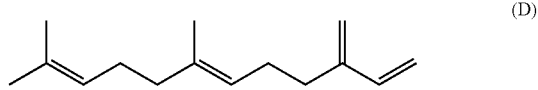
(D)

There is therefore a need for a catalyst system which permits the regioselective hydroformylation of 2-substituted butadienes in the delta-position without isomerization of the second double bond. In other words, as far as possible only the vinyl group —CH=CH$_2$ should be subjected to the hydroformylation, H. V. Barros, C. C. Guimaraes, E. N. dos Santos and E. V. Gusevskaya describe the hydroformylation of isoprene in Organometallics, 2007, 26, 2211-2218. When using Rh/triphenylphosphine as catalyst, 3-methyl-pent-3-enal and 3-methyl-pent-2-enal are described as main products. When using Rh/diphosphine systems, e.g. 1,2-bis(diphenylphosphino)ethane, 1,3-bis(diphenylphosphino)propane and 1,4-bis(diphenyl-phosphino)butane, the main product is 3-methyl-pent-2-enal, and up to 35% 4-methyl-pent-4-enal, inter alia, are found as by product.

In Organometallics 2008, 27, 4523-4531, H. V. Barros, J. G. da Silva, C. C. Guimaraes, E. N. dos Santos and E. V. Gusevskaya describe the hydroformylation of ß-myrcene using Rh/PPh$_3$ and Rh/PCy$_3$ as catalyst. For conversions of up to 98% and selectivities of 77%, 3-ethylidene-7-methyl-oct-6-enal is obtained as main product.

C. M. Foca, H. J. V. Barros, E. N. dos Santos, E. V. Gusevskaya, J. C. Baylon, New J. Chem., 2003, 27, 533-539 describes the hydroformylation of ß-myrcene with Pt/Sn catalysts and rhodium catalysts. When using Pt/Sn as catalyst, the hydroformylation product in the delta-position, i.e. 8-methyl-4-methylene-non-7-enal, is formed as the main product with a selectivity of up to 74% irrespective of the phosphorus ligand used. However, the yields are at most 40.7%. This document further reports on the use of Rh-phosphine, diphosphine and Rh-diphosphite catalyst systems. However, these do not have the same performance for the preparation of 8-methyl-4-methylene-non-7-enal as the described Pt/Sn catalysts. A disadvantage of the Pt/Sn catalysts used is that, on account of their chlorine content, they lead to corrosion problems and are therefore not very suitable for use on an industrial scale. There is therefore a need for a rhodium catalyst system which permits the hydroformylation of ß-myrcene (and comparable olefins) at least with the same regioselectivity as Pt/Sn catalysts.

WO 2010/033976 describes the preparation of detergent alcohol mixtures of polybranched polyolefins. ß-Myrcene and ß-farnesene, inter alia, are specified as possible polyolefin starting materials. The polyolefins are subjected to a hydroformylation and subsequent hydrogenation to give polybranched alcohols. In synthesis example III, ß-farnesene is hydroformylated using an Rh/xantphos/triphenylphosphine catalyst system and the reaction product is then hydrogenated. In the reaction product, 39% 4,8,12-trimethyl-tridecan-1-ol and 34% 3-ethyl-7,11-dimethyl-dodecan-1-ol are present; the discharge from the hydroformylation was not investigated.

It is therefore firstly the object of the present invention to provide a process for the regioselective hydroformylation of 2-substituted butadiene systems in which a product mixture is obtained which comprises, as main product, the product of the hydroformylation in the delta-position without isomerization of the second double bond. In other words, the catalyst system used should permit as selective as possible a hydroformylation of the vinyl double bond in high yield. In a specific embodiment, the object of the invention is to provide a process for the regioselective hydroformylation of trans-ß-farnesene in which a product mixture is obtained which comprises (7E)-8,12-dimethyl-4-methylenetrideca-7,11-dienal as main product. For this, the catalyst system used should be based on rhodium and as far as possible have no corrosive ligands.

(7E)-8,12-Dimethyl-4-methylenetrideca-7,11-dienal is an important synthesis building block and a potentially important intermediate in the synthesis of (3E,7E)-homo-farnesol:

Various processes for the preparation of (3E,7E)-homofarnesol are described in the literature:

It is in principle possible to prepare stereoisomerically pure (3E,7E)-homofarnesol starting from (E,E)-farnesol via (E,E)-farnesal, C1-extension according to Wittig with methylenetriphenylphosphorane and subsequent terminal hydroboration of the conjugated diene. However, this synthesis is very complex and a sensible route to (3E,7E)-homofarnesol neither from a technical point of view nor in terms of costs.

A. F. Barrero et al., J. Org. Chem. 1996, 61, 2215 (2) describes the synthesis of (3E,7E)-homofarnesol via the following reaction steps: a) distillative separation of (E/Z)-nerolidol, b) reaction of (E)-nerolidol with dimethylformamide dimethylacetal (DMFDMA) in a Büchi rearrangement to give the corresponding (3E/Z 7E)-C16-amides, c) flash chromatographic separation of the stereoisomeric amides and d) reduction of the (3E,7E)-amide to give the corresponding (3E,7E)-homofarnesol with lithium triethylborohydride.

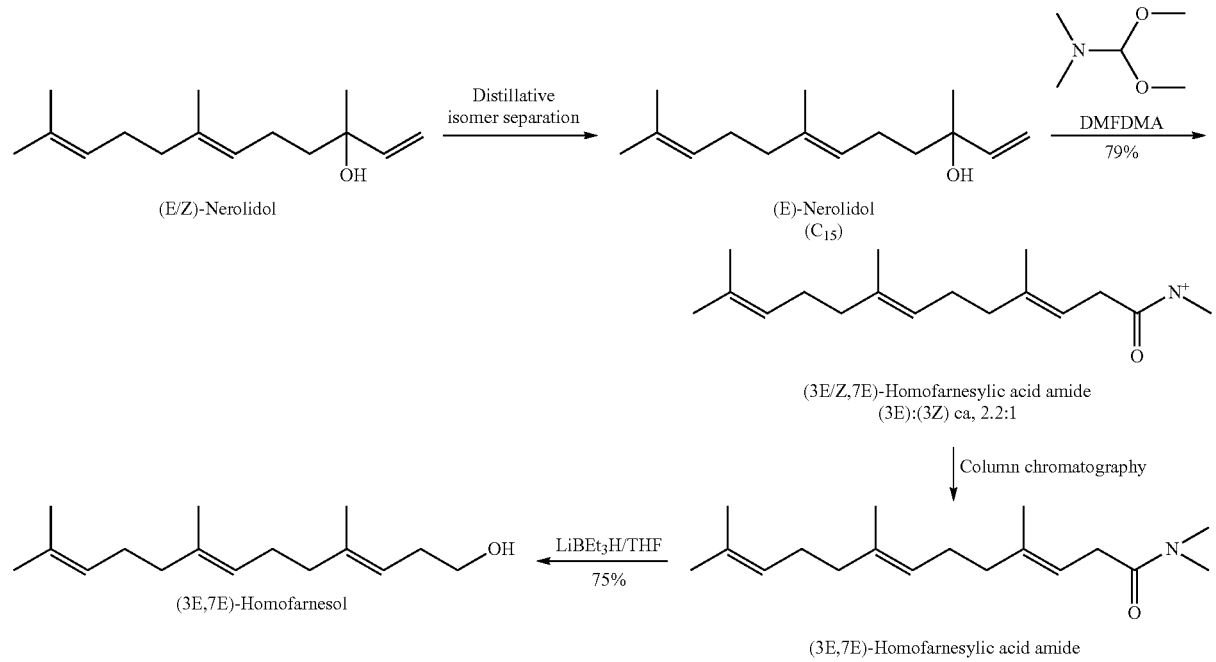

Disadvantages of this route are the moderate yields and the required flash chromatography for the separation of the stereoisomers.

WO 92/06063 describes a process for the preparation of α,β,γ-unsaturated carboxylic acids by carbonylation of the corresponding allylic alcohols, e.g. the carbonylation of (E)-nerolidol with the addition of catalytic amounts of palladium (II) chloride.

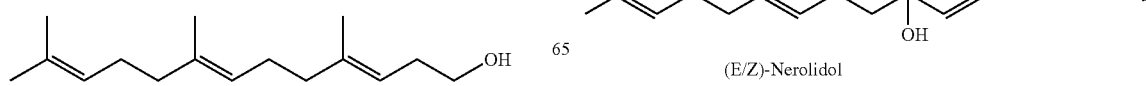

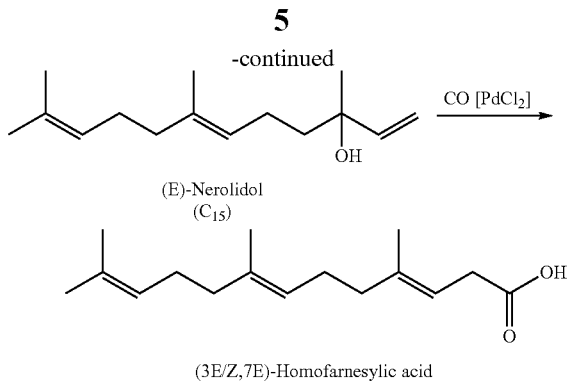

(E)-Nerolidol
($C_{15}$)

(3E/Z,7E)-Homofarnesylic acid

Also described is the reduction of the carbonylation product thus obtained to homofarnesol or monocyclohomofarnesol and the acid-catalyzed cyclization to give 3a,6,6,9a-tetramethyldodecahydronaphtho-[2,1-b]uran, an ambergris-like fragrance. A disadvantage of this process is the use of the relatively expensive palladium halides. Furthermore, the carbonylation reaction takes place at high CO pressures of ca. 70 bar.

WO 2013/156398 describes a process for the preparation of compounds of the general formula (E)

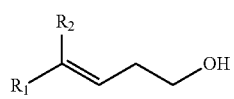

in which
$R_1$ is a straight-chain or branched, optionally mono- or polyunsaturated hydrocarbyl radical, and $R_2$ is H or $C_1$-$C_6$-alkyl, wherein
a) a carbonyl compound of the formula (F)

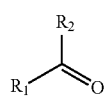

in which $R_1$ and $R_2$ have the meanings given above, is reacted by means of Wittig olefination to give a cyclopropane of the general formula (G)

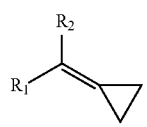

in which $R_1$ and $R_2$ have the meanings given above,
b) the cyclopropane of the formula (G) is reacted with ring opening to give a compound of the formula (H)

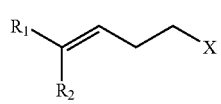

in which $R_1$ and $R_2$ have the meanings given above and X is halogen or O—R', in which R' is H, acyl, Tf-acetyl or SO2-R", in which R" is alkyl or aryl; and
c) the compound of the general formula (H) is converted to the compound of the general formula (E).

The preparation of homofarnesol, in particular (3E,7E)-homofarnesol from geranyl acetone (i.e. a $C_{13}$ building block) and cyclopropylphosphonium salt (i.e. a $C_3$ building block) in a Wittig reaction, inter alia, is described. The (E)-$C_{16}$ cyclopropane can be opened in the presence of an acid, e.g. a Lewis acid such as $AlCl_3$ or $BF_3$*$Et_2O$, and a nucleophile in a regio- and stereoselective manner to give homofarnesyl derivates. Then, the homofarnesyl chloride can be converted to the homofarnesol by acetate substitution and hydrolysis. Alternatively, the homofarnesol can be synthesized starting from homofarnesyl chloride via the formate and subsequent hydrolysis.

The syntheses described above for the preparation of (3E,7E)-homofarnesol are complex overall since they require several synthesis steps using costly reagents and/or drastic reaction conditions. A further object of the present invention is therefore to provide a process for the synthesis of (3E,7E)-homofarnesol using (7E)-8,12-dimethyl-4-methylenetrideca-7,11-dienal as intermediate which avoids the disadvantages described above.

Homofarnesol is for its part an important intermediate of synthesis processes for the preparation of Ambrox®. In particular, the cyclization of (3E,7E)-homofarnesol produces diastereomerically pure or enantiomerically pure Ambrox®. Ambrox® is the trade name of the enantiomerically pure compound (−)-ambrox (3aR,5aS,9aS,9bR)-3a,6,6,9a-tetramethyldodecahydronaphtho[2,1-b]furan, a valued odorant. Naturally occurring (−)-ambrox is the olfactorily most important ingredient of ambergris, a digestive product of sperm whales.

The cyclization of (3E,7E)-homofarnesol to ambrox is known per se, with both enzymatic and chemical cyclizations being described.

Thus, for example, the enzymatic cyclization by means of squalene hopene cyclase is known from WO 2010/139719.

Chemical cyclization reactions using a super acid (fluorosulfonic acid in 2-nitropropane) are known e.g. from P. F. Vlad et al. *Khimiya Geterotsiklicheskikh Soedinenii, Engl. Transl.* 1991, 746. Further processes comprise the enantioselective polyene cyclization of homofarnesyl triethyl silyl ether in the presence of O-(o-fluorobenzyl)binol and $SnCl_4$, as described by H. Yamamoto et al. *J. Am. Chem. Soc.* 2002, 3647.

It is therefore a further object of the present invention to provide a process for the synthesis of ambrox using (7E)-8,12-dimethyl-4-methylenetrideca-7,11-dienal and (3E,7E)-homofarnesol as intermediates.

Surprisingly, it has now been found that, using rhodium catalysts with specific phosphorus chelate compounds as ligands, the regioselective hydroformylation of 2-substituted butadiene systems is successful, giving a product mixture which comprises, as main product, the product of the hydroformylation of the vinyl double bond without isomerization of the second double bond. If the starting materials used for the hydroformylation comprise further internal double bonds besides the butadiene system, then these are essentially neither hydroformylated nor isomerized. The phosphorus chelate compounds used as ligands of the hydroformylation catalysts have rigid backbones, i.e. the bridging group to which the phosphorus atoms are bonded (generally via an oxygen atom) is not capable of free rotation. Moreover, the bite angle of the phosphorus chelate ligands is preferably about 120°. With these rhodium catalysts having specific phosphorus chelate compounds as ligands, the hydroformylation of trans-beta-farnesene is advantageously successful, giving (7E)-8,12-dimethyl-4-methylenetrideca-7,11-dienal as main product. This can be further reacted in accordance with the invention to give (−)-ambrox.

SUMMARY OF THE INVENTION

The invention firstly provides a process for the preparation of compounds of the general formula (I) and of secondary products thereof,

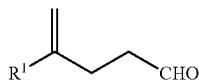
(I)

comprising at least one reaction step, in which at least one compound of the general formula (II)

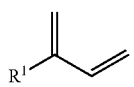
(II)

in which

R¹ is in each case linear or branched $C_1$-$C_{24}$-alkyl or $C_2$-$C_{24}$-alkenyl having 1, 2, 3 or more than 3 C—C double bonds, is subjected to a reaction with carbon monoxide and hydrogen in the presence of a hydroformlyation catalyst which comprises a rhodium complex with at least one phosphorus chelate compound as ligand, wherein a reaction mixture is obtained which comprises at least 50.1% by weight, based on the total weight of the reaction mixture, of at least one compound of the general formula (I).

The invention further provides a process for the hydroformylation in which trans-β-farnesene is subjected to a reaction with carbon monoxide and hydrogen in the presence of a hydroformylation catalyst which comprises a rhodium complex with at least one phosphorus chelate compound as ligand, as defined above and below, wherein a reaction mixture is obtained which comprises at least 50.1% by weight, based on the total weight of the reaction mixture, of (7E)-8,12-dimethyl-4-methylenetrideca-7,11-dienal.

The invention further provides a process in which
a) at least one compound of the general formula (II)

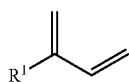
(II)

in which

R¹ is in each case linear or branched $C_1$-$C_{24}$-alkyl or $C_2$-$C_{24}$-alkenyl having 1, 2, 3 or more than 3 C—C double bonds, is subjected to a reaction with carbon monoxide and hydrogen in the presence of a hydroformylation catalyst which comprises a rhodium complex with at least one phosphorus chelate compound as ligand, wherein a reaction mixture is obtained which comprises at least 50.1% by weight, based on the total weight of the reaction mixture, of at least one compound of the general formula (I), b) the reaction mixture obtained in step a) or a fraction thereof enriched in at least one compound of the general formula (I) is subjected to a hydrogenation, wherein a reaction mixture is obtained which comprises at least one compound of the general formula (III)

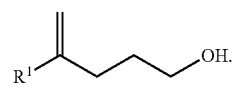
(III)

The invention further provides a process in which
a) at least one compound of the general formula (II)

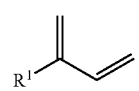
(II)

in which

R¹ is in each case linear or branched $C_1$-$C_{24}$-alkyl or $C_2$-$C_{24}$-alkenyl having 1, 2, 3 or more than 3 C—C double bonds, is subjected to a reaction with carbon monoxide and hydrogen in the presence of a hydroformylation catalyst which comprises a rhodium complex with at least one phosphorus chelate compound as ligand, wherein a reaction mixture is obtained which comprises at least 50.1% by weight, based on the total weight of the reaction mixture, of at least one compound of the general formula (I), b) the reaction mixture obtained in step a) or a fraction thereof enriched in at least one compound of the general formula (I) is subjected to a hydrogenation, wherein a reaction mixture is obtained which comprises at least one compound of the general formula (III),

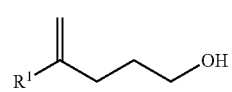
(III)

c) the at least one compound of the general formula (III) is subjected to an at least partial isomerization to give a compound of the general formula (IV)

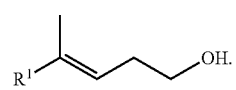
(IV)

The invention further provides a process for the preparation of (−)-ambrox (V)

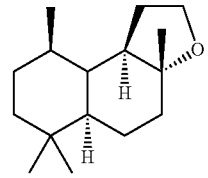
(V)

in which a1) (6E)-7,11-dimethyl-3-methylidenedodeca-1,6,10-triene (II.1)

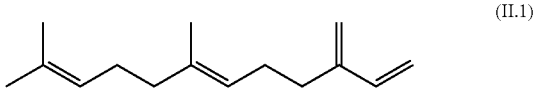

(II.1)

is subjected to a reaction with carbon monoxide and hydrogen in the presence of a hydroformylation catalyst which comprises a rhodium complex with at least one phosphorus chelate compound as ligand, wherein a reaction mixture is obtained which comprises at least 50.1% by weight, based on the total weight of the reaction mixture, of (7E)-8,12-dimethyl-4-methylenetrideca-7,11-dienal (I.1),

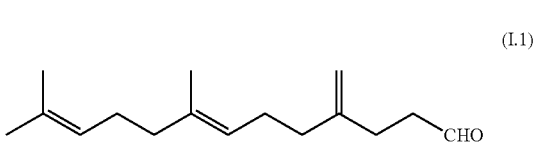 [SMILES: C=C(CCC=O)CC/C=C(\C)CCC=C(C)C]

(I.1)

b1) the reaction mixture obtained in step a) or a fraction thereof enriched in at least one compound of the general formula (I.1) is subjected to a hydrogenation, wherein a reaction mixture is obtained which comprises the compound (III.1),

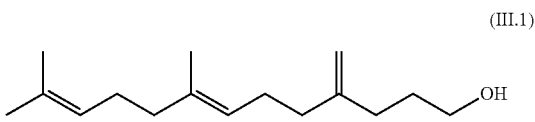

(III.1)

c1) the compound (III.1) is subjected to an at least partial isomerization, giving (3E,7E)-homofarnesol (IV.1),

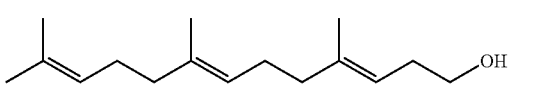

(IV.1)

d1) the (3E,7E)-homofarnesol (IV.1) is subjected to a cyclization to give (−)-ambrox (V).

DESCRIPTION OF THE INVENTION

In the compounds of the general formula (I.2)

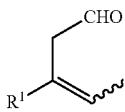

(I.2)

the wavy bond is intended to indicate that it can be the pure cis isomer, the pure trans isomer or any desired cis/trans mixture.

The following details relating to suitable and preferred embodiments of the hydroformylation of at least one compound of the general formula (II) to give a reaction mixture which comprises at least 50.1% by weight of at least one compound of the general formula (I) apply equally to the embodiment of the invention according to which the compound (I) is the end product as well as to the embodiments according to which the compound (I) is an intermediate. If the compound (I) is an intermediate, this reaction step is also referred to as "step a)".

The following details relating to suitable and preferred embodiments in the case of reaction step a) apply analogously to the reaction step a1), unless specific details are given. The following details relating to suitable and preferred embodiments in the case of reaction step b) apply analogously to the reaction step b1) unless specific details are given. The following details relating to suitable and preferred embodiments in the case of reaction step c) apply analogously to the reaction step c1) unless specific details are given.

Hydroformylation (Step a))

Preferably, the compounds of the formula (I) have only one vinyl group, i.e. only one group of the formula —CH═CH$_2$ in the molecule.

The compounds of the formula (II) are particularly preferably selected from isoprene, β-myrcene and β-farnesene. A particularly preferred compound of the formula (II) is (6E)-7,11-dimethyl-3-methylidendodeca-1,6,10-triene (=trans-β-farnesene).

In a specific embodiment, β-farnesene is subjected to a hydroformylation in the process according to the invention.

The process according to the invention permits the hydroformylation of compounds of the general formula (I) with high yield and with high selectivity.

The conversion of the compounds of the general formula (I) is generally at least 65%, preferably at least 80%, particularly at least 85%, in particular at least 90%, based on the amount of compounds of the general formula (I) used. An even higher conversion can be attained with selected ligands.

The selectivity as regards the compounds of the general formula (II.1) is generally at least 55%, preferably at least 60%, particularly at least 65%, in particular at least 70%, based on the reacted amount of compounds of the general formula (I). An even higher selectivity can be attained with selected ligands.

Preferably, a reaction mixture is obtained by the process according to the invention which comprises at least 55% by weight, preferably at least 60%, in particular at least 65% by weight, based on the total weight of the reaction mixture, of at least one compound of the general formula (II.1). An even higher conversion can be achieved with selected ligands.

Preferably, the reaction mixture obtained by the process according to the invention comprises in total at most 49.9% by weight, preferably at most 45% by weight, in particular at most 40% by weight, specifically at most 35% by weight, of compounds which are selected from the compound of the general formula (I.2)

(I.2)

in which R$^1$ is in each case linear or branched C$_1$-C$_{24}$-alkyl, or C$_2$-C$_{24}$-alkenyl having 1, 2, 3 or more than 3 C—C double bonds, and optionally further compounds different from the compounds (I) and (I.2). Further compounds different from the compounds (I) and (I.2) can result by virtue of hydroformylation of a different double bond instead of or in addition to the terminal vinyl group, isomerization of at least one double bond, hydrogenation of at least one double bond, and combinations of at least two of these reactions. An overview of the products obtained during the hydroformylation of myrcene is given by C. M. Foca et al., New J. Chem., 2003, 27, 533-539 in scheme 1 on page 533.

Preferably, the hydroformylation catalyst used has at least one bidentate phosphorus chelate compound as ligands which have a natural bite angle in the region of about 120°. The expression "natural bite angle" is understood here in the customary specialist way, as is defined e.g. in P. W. N. M. van Leeuwen et al., Chem. Rev. 2000, 2741.

According to the invention, a catalyst is used which comprises rhodium as metal.

Hereinbelow, the expression "alkyl" comprises straight-chain and branched alkyl groups. Preferably, these are straight-chain or branched $C_1$-$C_{20}$-alkyl, preferably $C_1$-$C_{12}$-alkyl, particularly preferably $C_1$-$C_8$-alkyl and very particularly preferably $C_1$-$C_6$ alkyl groups. Examples of alkyl groups are in particular methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also comprises substituted alkyl groups which can carry generally 1, 2, 3, 4 or 5, preferably 1, 2 or 3 and particularly preferably 1, substituent(s) selected from the groups cycloalkyl, aryl, hetaryl, halogen, $NE^1E^2$, $NE^1E^2E^{3-}$, COOH, carboxylate, $SO_3H$ and sulfonate. A preferred fluorinated alkyl group is trifluoromethyl. The expression "alkyl" also comprises alkyl groups which are interrupted by one or more nonadjacent oxygen atoms, preferably alkoxyalkyl.

In the context of the present invention, the expression "alkylene" is straight-chain or branched alkanediyl groups having preferably 1 to 6 carbon atoms. These include methylene (—$CH_2$—), ethylene (—$CH_2$—$CH_2$—), n-propylene (—$CH_2$—$CH_2$—$CH_2$—), isopropylene (—$CH_2$—$CH(CH_3)$—), etc.

In the context of the present invention, the expression "cycloalkyl" comprises unsubstituted as well as substituted cycloalkyl groups, preferably $C_5$-$C_7$-cycloalkyl groups, such as cyclopentyl, cyclohexyl or cycloheptyl, which in the case of a substitution can carry generally 1, 2, 3, 4 or 5, preferably 1, 2 or 3 and particularly preferably 1 substituent(s) selected from the groups alkyl, alkoxy and halogen.

In the context of the present invention, the expression "heterocycloalkyl" comprises saturated or partially unsaturated cycloaliphatic groups having in general 4 to 7, preferably 5 or 6 ring atoms in which 1, 2, 3 or 4 of the ring carbon atoms are replaced by heteroatoms, preferably selected from the elements oxygen, nitrogen and sulfur, and which can be optionally substituted. In the case of a substitution, these heterocycloaliphatic groups have preferably 1, 2 or 3, particularly preferably 1 or 2, in particular 1 substituent(s). These are preferably selected from alkyl, cycloalkyl, aryl, COOR (R=H, alkyl, cycloalkyl, aryl), $COO^-M^+$ and $NE^1E^2$, preferably alkyl. By way of example of such heterocycloaliphatic groups, mention may be made of pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydro-thiophenyl, tetrahydrofuranyl, tetrahydropyranyl, dioxanyl.

In the context of the present invention, the expression "aryl" comprises both unsubstituted as well as substituted aryl groups, and is preferably phenyl, tolyl, xylyl, mesityl, naphthyl, fluorenyl, anthracenyl, phenanthrenyl or naphthacenyl, particularly preferably phenyl or naphthyl. In the case of a substitution, these aryl groups can carry generally 1, 2, 3, 4 or 5, preferably 1, 2 or 3 and particularly preferably 1 substituent(s). These are preferably selected from the groups alkyl, alkoxy, carboxyl, carboxylate, trifluoromethyl, —$SO_3H$, sulfonate, $NE^1E^2$, alkylene-$NE^1E^2$, nitro, cyano or halogen. A preferred fluorinated aryl radical is pentafluorophenyl.

In the context of the present invention, the expression "hetaryl" comprises unsubstituted or substituted, heterocycloaromatic groups, preferably the groups pyridyl, quinolinyl, acridinyl, pyridazinyl, pyrimidinyl, pyrazinyl, and the subgroup of the "pyrrole group", where these heterocycloaromatic groups in the case of a substitution can carry generally 1, 2 or 3 substituents selected from the groups alkyl, alkoxy, carboxyl, carboxylate, —$SO_3H$, sulfonate, $NE^1E^2$, alkylene-$NE^1E^2$, trifluoromethyl or halogen.

In the context of the present invention, the expression "pyrrole group" is a series of unsubstituted or substituted, heterocycloaromatic groups which are derived structurally from the pyrrole basic backbone and comprise a pyrrolic nitrogen atom in the heterocycle which can be covalently bonded to other atoms, for example a phosphorus atom. The expression "pyrrole group" thus comprises the unsubstituted or substituted groups pyrrolyl, imidazolyl, pyrazolyl, indolyl, purinyl, indazolyl, benzotriazolyl, 1,2,3-triazolyl, 1,3,4-triazolyl and carbazolyl, which, in the case of a substitution, can carry generally 1, 2 or 3, preferably 1 or 2, particularly preferably 1, substituent(s) selected from the groups alkyl, alkoxy, formyl, acyl, carboxyl, carboxylate, —$SO_3H$, sulfonate, $NE^1E^2$, alkylene-$NE^1E^2$, trifluoromethyl or halogen. A preferred substituted indolyl group is the 3-methylindolyl group.

Accordingly, the expression "bispyrrole group" in the context of the present invention comprises divalent groups of the formula Py-I-Py, 

which comprise two pyrrole groups bonded by direct chemical bond or alkylene groups, —O—, —S—, imino-, silyl- or alkylimino-group-mediated linkage, such as the bisindolyl group of the formula

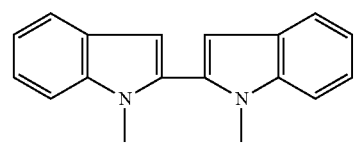 [SMILES: Cn1c(-c2cc3ccccc3n2C)cc2ccccc21]

as an example of a bispyrrole group which comprises two directly linked pyrrole group-, in this case indolyl, or the bispyrrolediylmethane group of the formula

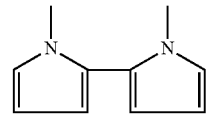

as an example of a bispyrrole group which comprises two pyrrole groups linked via a methylene group, in this case pyrrolyl. Like the pyrrole groups, the bispyrrole groups can also be unsubstituted or substituted and, in the case of a substitution, carry per pyrrole group unit in general 1, 2 or 3, preferably 1 or 2, in particular 1 substituent(s) selected from alkyl, alkoxy, carboxyl, carboxylate, —SO₃H, sulfonate, NE¹E², alkylene-NE¹E², trifluoromethyl or halogen, where, for these details relating to the number of possible substitutents, the linkage of the pyrrole group units by direct chemical bond or by the linkage mediated by means of the aforementioned groups is not considered to be substitution.

In the context of this invention, carboxylate and sulfonate are preferably a derivative of a carboxylic acid function or of a sulfonic acid function, respectively, in particular a metal carboxylate or sulfonate, a carboxylic acid or sulfonic acid ester function or a carboxylic acid or sulfonic acid amide function. These include e.g. the esters with $C_1$-$C_4$-alkanols, such as methanol, ethanol, n-propanol, isopropanol, n-butanol, sec-butanol and tert-butanol. These also include the primary amides and the N-alkyl and N,N-dialkyl derivates thereof.

The above explanations with regard to the expressions "alkyl", "cycloalkyl", "aryl" "heterocycloalkyl" and "hetaryl" apply accordingly to the expressions "alkoxy", "cycloalkoxy", "aryloxy", "heterocycloalkoxy" and "hetaryloxy".

In the context of the present invention, the expression "acyl" is alkanoyl or aroyl groups having in general 2 to 11, preferably 2 to 8, carbon atoms, for example the acetyl, propanoyl, butanoyl, pentanoyl, hexanoyl, heptanoyl, 2-ethylhexanoyl, 2-propyl-heptanoyl, benzoyl or naphthoyl group.

The groups $NE^1E^2$, $NE^4E^5$, $NE^7E^8$, $NE^8E^{18}$ and $NE^{12}E^{13}$ are preferably N,N-dimethyl-amino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine and iodine, preferably fluorine, chlorine and bromine.

M⁺ is a cation equivalent, i.e. a monovalent cation or the fraction of a polyvalent cation corresponding to a single positive charge. The cation M⁺ serves merely as counterion to neutralize negatively charged substituent groups, such as the COO or the sulfonate group, and can in principle be selected as desired. Preference is therefore given to using alkali metal ions, in particular Na⁺, K⁺, Li⁺ ions or onium ions, such as ammonium, mono-, di-, tri-, tetraalkylammonium, phosphonium, tetraalkylphosphonium or tetraarylphosphonium ions.

The same applies to the anion equivalent X⁻, which serves merely as counterion of positively charged substituent groups, such as the ammonium groups, and can be selected as desired among monovalent anions and the fractions of a polyvalent anion corresponding to a single negative charge. Suitable anions are e.g. halide ions X⁻, such as chloride and bromide. Preferred anions are sulfate and sulfonate, e.g. $SO_4^{2-}$, tosylate, trifluoromethanesulfonate and methylsulfonate.

The values for y are an integer from 1 to 120, preferably an integer from 3 to 120.

Condensed ring systems can be aromatic, hydroaromatic and cyclic compounds linked (fused) by annelation. Condensed ring systems consist of two, three or more than three rings. Depending on the type of linkage, a distinction is made in the case of condensed ring systems between an ortho annelation, i.e. each ring has one edge and/or two atoms in common with each adjacent ring in each case, and a peri annelation, in which a carbon atom belongs to more than two rings. Among the condensed ring systems, preference is given to ortho-condensed ring systems.

In the context of the invention, the expression phosphorus chelate compound refers specifically to a compound in which at least two phosphorus-atom-containing groups are covalently bonded to one and the same molecular backbone. The individual atoms of the molecular backbone are here likewise joined together via covalent bonds.

The rhodium complexes having at least one phosphorus chelate compound as ligands used as hydroformylation catalysts are known in principle and are described e.g. in WO 01/58589, WO 02/083695, WO 02/22261, WO 03/018192, WO 2004/026803, WO 2005/009934, WO 2005/039762, WO 2005/063730 and DE 103 42 760 A1.

Preferably, the hydroformylation catalyst used comprises at least one phosphorus chelate compound of the general formula (VI)

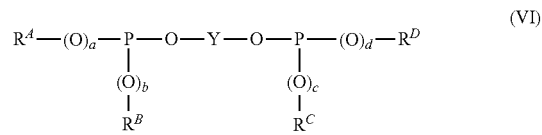

in which
$R^A$, $R^B$, $R^C$ and $R^D$, independently of one another, are alkyl, cycloalkyl, heterocycloalkyl, aryl or hetaryl,
where the alkyl radicals $R^A$, $R^B$, $R^C$ and $R^D$ are unsubstituted or carry 1, 2, 3, 4 or 5 identical or different substituents which are selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, COOH, carboxylate, SO₃H, sulfonate, $NE^1E^2$, $NE^1E^2E^{3+}X^-$, halogen, nitro, formyl, acyl and cyano, in which $E^1$, $E^2$ and $E^3$ are in each case identical or different radicals selected from hydrogen, alkyl, cycloalkyl or aryl, and $X^-$ is an anion equivalent,
and where the cycloalkyl, heterocycloalkyl, aryl and hetaryl radicals $R^A$, $R^B$, $R^C$ and $R^D$ are in each case unsubstituted or carry 1, 2, 3, 4 or 5 identical or different substituents which are selected from alkyl and the substituents specified above for the alkyl radicals $R^A$, $R^B$, $R^C$ and $R^D$,
or
$R^A$ and $R^B$ and/or $R^C$ and $R^D$, together with the phosphorus atom and, if present, the oxygen atoms to which they are bonded, are a 5- to 8-membered heterocycle which is optionally additionally annelated once, twice or three times with cycloalkyl, heterocycloalkyl, aryl or hetaryl, where the heterocycle and, if present, the annelated groups are, independently of one another, unsubstituted or carry one, two, three or four identical or different substituents which are selected from alkyl, cycloalkyl, heterocycloalkyl, aryl, hetaryl, hydroxy, mercapto, polyalkylene oxide, polyalkyleneimine, alkoxy, halogen, COOH, carboxylate, SO₃H, sulfonate, $NE^4E^6$, $NE^4E^6E^{6+}X^-$, nitro, alkoxycarbonyl, formyl, acyl and cyano, in which $E^4$, $E^5$ and $E^6$ are in each case identical or different radicals, selected from hydrogen, alkyl, cycloalkyl and aryl, and X⁻ is an anion equivalent, a, b, c and d, independently of one another, are 0 or 1, and Y is selected from groups of the formula VII.a or VII.b

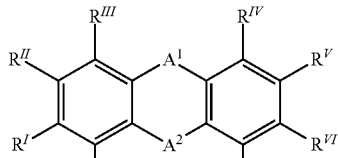

(VII.a)

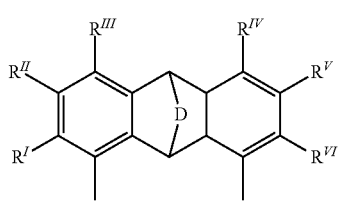

(VII.b)

in which
$R^I$, $R^{II}$, $R^{III}$, $R^{IV}$, $R^V$ and $R^{VI}$, independently of one another, are hydrogen, alkyl, cycloalkyl, heterocycloalkyl, aryl, hetaryl, hydroxy, mercapto, polyalkylene oxide, polyalkyleneimine, alkoxy, halogen, SO3H, sulfonate, $NE^7E^8$, alkylene-$NE^7E^8$, trifluoromethyl, nitro, alkoxycarbonyl, carboxyl, formyl, acyl or cyano, in which $E^7$ and $E^8$ are in each case identical or different radicals selected from hydrogen, alkyl, cycloalkyl and aryl, where two adjacent radicals $R^I$ to $R^{VI}$, together with the carbon atoms of the benzene ring to which they are bonded, can also be a condensed ring system having 1, 2 or 3 further rings, $A^1$ and $A^2$, independently of one another, are O, S, $SiR^ER^F$, $NR^G$ or $CR^HR^K$, where $R^E$, $R^F$, $R^G$, $R^H$ and $R^K$, independently of one another, are hydrogen, alkyl, cycloalkyl, heterocycloalkyl, aryl or hetaryl, and D is a divalent bridging group of the general formula

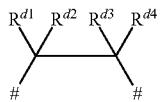

in which
# is in each case a binding site to the 9,10-dihydroanthracene backbone, and $R^{d1}$, $R^{d2}$, $R^{d3}$ and $R^{d4}$, independently of one another, are hydrogen, alkyl, cycloalkyl, aryl, halogen, trifluoromethyl, carboxyl, carboxylate or cyano, where $R^{d1}$ can also be, together with $R^{d3}$, the binding fraction of a double bond between the two carbon atoms to which $R^{d1}$ and $R^{d3}$ are bonded, and/or $R^{d2}$ and $R^{d4}$, together with the carbon atoms to which they are bonded, can also be a 4- to 8-membered carbo- or heterocycle, which is optionally additionally annelated once, twice or three times with cycloalkyl, heterocycloalkyl, aryl or hetaryl, where the carbo- or heterocycle and, if present, the annelated groups are, independently of one another, unsubstituted or in each case carry one, two, three or four identical or different substituents which are selected from alkyl, cycloalkyl, heterocycloalkyl, aryl, hetaryl, $COOR^{d5}$, $COO^-M^+$, $SO_3R^{d5}$, $SO_3^-M^+$, $NE^9E^{10}$, alkylene-$NE^9E^{10}$, $NE^9E^{10}E^{11+}X^-$, alkylene-$NE^9E^{10}E^{11+}X^-$, $OR^{d6}$, $SR^{d6}$, $(CHR^+CH_2O)_yR^{d6}$, $(CH_2N(E^9))_yR^{d6}$, $(CH_2CH_2N(E^9))_y$ $R^{d6}$, halogen, trifluoromethyl, nitro, formyl, acyl or cyano, in which $R^{d5}$, $E^9$, $E^{10}$ and $E^{11}$ are in each case identical or different radicals selected from hydrogen, alkyl, cycloalkyl or aryl, $R^{d6}$ is hydrogen, methyl or ethyl, $M^+$ is a cation equivalent, $X^-$ is an anion equivalent, and y is an integer from 1 to 120.

Preferably, in the compounds of the formula (VI), the radicals $R^A$, $R^B$, $R^C$ and $R^D$ all have the same meaning.

Preferably, the bridging group Y is a group of the formula VII.a, in which the groups $A^1$ and $A^2$ are selected from the groups O, S and $CR^HR^K$, in particular from O, S, the methylene group ($R^H=R^K=H$), the dimethylmethylene group ($R^H=R^K=CH_3$), the diethylmethylene group ($R^H=R^K=C_2H_5$), the di-n-propyl-methylene group ($R^H=R^K=$n-propyl) or the di-n-butylmethylene group ($R^H=R^K=$n-butyl). In particular, preference is given to those bridging groups Y in which $A^1$ is different from $A^2$, with $A^1$ preferably being a $CR^HR^K$ group and $A^2$ preferably being an O or S group, particularly preferably an oxa group O.

Further preferably, the bridging group Y is a group of the formula VII.b, in which D is a divalent bridging group which is selected from the groups

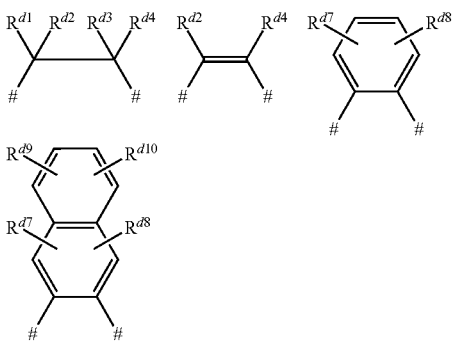

in which $R^{d1}$, $R^{d2}$, $R^{d3}$ and $R^{d4}$, independently of one another, are hydrogen, alkyl, cycloalkyl, aryl, halogen, trifluoromethyl, carboxyl, carboxylate or cyano or are joined together to give a $C_3$-$C_4$-alkylene group, and $R^{d7}$, $R^{d8}$, $R^{d9}$ and $R^{d10}$, independently of one another, can be hydrogen, alkyl, cycloalkyl, aryl, halogen, trifluoromethyl, COOH, carboxylate, cyano, alkoxy, $SO_3H$, sulfonate, $NE^9E^{10}$, alkylene-NE9E10E11+X-, aryl or nitro. Preferably, the groups are hydrogen, $C_1$-$C_{10}$-alkyl or carboxylate and the groups $R^{d7}$, $R^{d8}$, $R^{d9}$ and $R^{d10}$ are hydrogen, $C_1$-$C_{10}$-alkyl, halogen, in particular fluorine, chlorine or bromine, trifluoromethyl, $C_1$-$C_4$-alkoxy, carboxylate, sulfonate or aryl. Particularly preferably, $R^{d7}$, $R^{d8}$, $R^{d9}$ and $R^{d10}$ are hydrogen.

Particularly preferred bridging groups D are the ethylene group and the 1,2-phenylene group.

A particularly preferred bridging group D is the ethylene group $-CH_2-CH_2-$. The bridging groups Y of the formula (VII.b) then preferably have a triptycene-like carbon backbone.

In the bridging groups Y of the formula VII.a and VII.b, the substituents $R^I$, $R^{II}$, $R^{III}$, $R^{IV}$, $R^V$ and $R^{VI}$ are preferably selected from hydrogen, alkyl, alkoxy, cycloalkyl, heterocycloalkyl, aryl and hetaryl.

According to a first preferred embodiment, $R^I$, $R^{II}$, $R^{III}$, $R^{IV}$, $R^V$ and $R^{VI}$ are all hydrogen.

According to a further preferred embodiment, $R^{II}$ and $R^V$, independently of one another, are $C_1$-$C_4$-alkyl or $C_1$-$C_4$-alkoxy and $R^I$, $R^{III}$, $R^{IV}$ and $R^{VI}$ are hydrogen. Preferably, $R^{II}$ and $R^V$ are selected from methyl, ethyl, isopropyl, tert-butyl and methoxy.

According to a further preferred embodiment, $R^I$ and $R^{VI}$, independently of one another, are $C_1$-$C_4$-alkyl or $C_1$-$C_4$-alkoxy and $R^{II}$, $R^{III}$, $R^{IV}$ and $V^V$ are hydrogen. Preferably, $R^I$ and $R^{VI}$ are selected from methyl, ethyl, isopropyl, tert-butyl and methoxy.

In particular, Y is a group of the formula (VII.a), in which $R^{II}$ and $R^V$ are in each case both methyl, ethyl, isopropyl or tert-butyl, and $R^I$, $R^{III}$, $R^{IV}$ and $R^{VI}$ are hydrogen.

In particular, Y is a group of the formula (VII.b) in which $R^I$, $R^{II}$, $R^{III}$, $R^{IV}$, $R^V$ and $R^{VI}$ are all hydrogen.

In a first preferred embodiment, the rhodium complexes used as hydroformylation catalysts have at least one chelate phosphoramidite as ligand. Particularly preferably, the hydroformylation catalyst used comprises at least one phosphorus chelate compound of the general formula (VI.1)

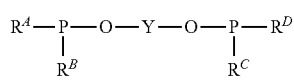
(VI.1)

in which
Y has the meaning given above, and
the radicals $R^A$, $R^B$, $R^C$ and $R^D$, independently of one another, are selected from pyrrole groups bonded to the phosphorus atom via the pyrrolic nitrogen atom.

Preferably, in the compounds of the general formula (VI.1), the radicals $R^A$ and $R^B$ and the radicals $R^C$ and $R^D$ are not joined together. The meaning of the term pyrrole group here corresponds to the definition given above.

Particularly preferably, the hydroformylation catalyst used comprises at least one phosphorus chelate compound of the general formula (VI.1)

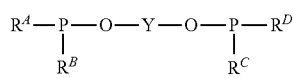
(VI.1)

in which
Y has the meaning given above, and
the radicals $R^A$, $R^B$, $R^C$ and $R^D$, independently of one another, are selected from groups of the formulae VIII.a to VIII.k

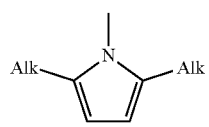
(VIII.a)

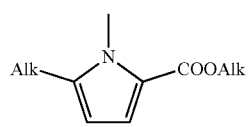
(VIII.b)

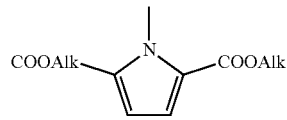
(VIII.c)

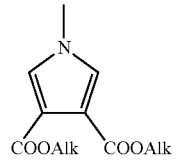
(VIII.d)

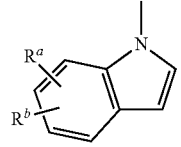
(VIII.e)

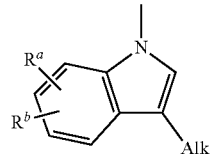
(VIII.f)

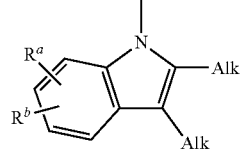
(VIII.g)

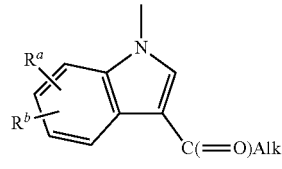
(VIII.h)

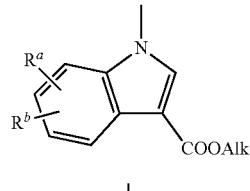
(VIII.i)

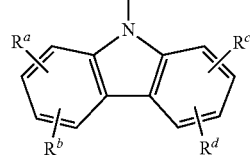
(VIII.k)

in which

Alk is a $C_1$-$C_4$-alkyl group and $R^a$, $R^b$, $R^c$ and $R^d$, independently of one another, are hydrogen, $C_1$-$C_4$-alkyl, $C_1$-$C_4$-alkoxy, formyl, acyl, halogen, $C_1$-$C_4$-alkoxycarbonyl or carboxyl.

Preferably, in the compounds of the formula (VI.1), the radicals $R^A$, $R^B$, $R^C$ and $R^D$ all have the same meaning.

Preferred alkyl radicals $R^a$ to $R^d$ in the compounds of the formula (VI.1) are methyl, ethyl, n-propyl, isopropyl, n-butyl, tert-butyl and trifluoromethyl.

In a specific embodiment, in the compounds of the formula (VI.1), the radicals $R^A$, $R^B$, $R^C$ and $R^D$ are the 3-methylindolyl group (skatolyl group).

In particular, in the compounds (VI.1), the group Y is a group of the formula (VII.a) in which $R^{II}$ and $R^V$ are in each case both methyl, ethyl, isopropyl or tert-butyl and $R^I$, $R^{III}$, $R^{IV}$ and $R^{VI}$ are hydrogen.

In a second preferred embodiment, the rhodium complexes used as hydroformylation catalysts have at least one chelate phosphite as ligand. Particularly preferably, the hydroformylation catalyst used comprises at least one phosphorus chelate compound of the general formula (VI.2)

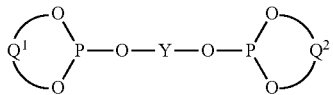
(VI.2)

in which

Y has the meaning given above, and $Q^1$ and $Q^2$, independently of one another, are a divalent bridging group of the general formula (IX),

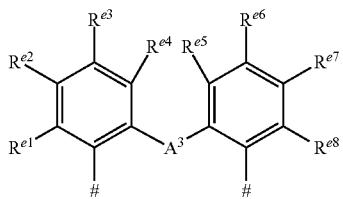
(IX)

in which

\# is in each case a binding site to the phosphite group, $R^{e1}$, $R^{e2}$, $R^{e3}$, $R^{e4}$, $R^{e5}$, $R^{e6}$, $R^{e7}$ and $R^{e8}$, independently of one another, are hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy, halogen, hydroxy, mercapto, cyano, nitro, formyl, acyl, carboxy, carboxylates, alkylcarbonyloxy, carbamoyl, sulfo, sulfonate or $NE^{12}E^{13}$, in which $E^{12}$ and $E^{13}$ are in each case identical or different radicals selected from hydrogen, alkyl, cycloalkyl, heterocycloalkyl, aryl or hetaryl, where two adjacent radicals $R^{e1}$ to $R^{e8}$, together with the carbon atoms of the benzene ring to which they are bonded, can also be a condensed ring system having 1, 2 or 3 further rings, and $A^3$ is a single bond, O, S, $NR^{a31}$, $SiR^{a32}R^{a33}$ or $C_1$-$C_4$-alkylene which can have a double bond and/or an alkyl, cycloalkyl, heterocycloalkyl, aryl or hetaryl substituent, or can be interrupted by O, S, $NR^{a31}$ or $SiR^{a32}R^{a33}$, where $R^{a31}$, $R^{a32}$ and $R^{a33}$, independently of one another, are hydrogen, alkyl, cycloalkyl, heterocycloalkyl, aryl or hetaryl.

Preferably, in the compounds (VI.2), at least one of the groups $Q^1$ or $Q^2$ is a group of the formula (IX), in which $A^3$ is a single bond, $R^{e1}$ and $R^{e8}$, independently of one another, are $C_1$-$C_4$-alkyl or $C_1$-$C_4$-alkoxy, and $R^{e2}$, $R^{e3}$, $R^{e4}$, $R^{e5}$, $R^{e6}$ and $R^{e7}$ are hydrogen. Preferably, $R^{e1}$ and $R^{e8}$, independently of one another, are selected from methyl, ethyl, isopropyl, tert-butyl and methoxy.

Preferably, in the compounds (VI.2), at least one of the groups $Q^1$ or $Q^2$ is a group of the formula (IX) in which $A^3$ is a single bond, $R^{e4}$ and $R^{e5}$, independently of one another, are $C_1$-$C_4$-alkyl or $C_1$-$C_4$-alkoxy, and $R^{e1}$, $R^{e2}$, $R^{e3}$, $R^{e6}$, $R^{e7}$ and $R^{e8}$ are hydrogen. Preferably, $R^{e4}$ and $R^{e5}$, independently of one another, are selected from methyl, ethyl, isopropyl, tert-butyl and methoxy.

Preferably, in the compounds (VI.2), at least one of the groups $Q^1$ or $Q^2$ is a group of the formula (IX) in which $A^3$ is a single bond, and $R^{e1}$, $R^{e2}$, $R^{e3}$, $R^{e4}$, $R^{e5}$, $R^{e6}$, $R^{e7}$ and $R^{e8}$ are hydrogen.

Particularly preferably, in the compounds (VI.2), at least one of the groups $Q^1$ or $Q^2$ is a group of the formula (IX) in which $A^3$ is a single bond, $R^{e1}$, $R^{e3}$, $R^{e6}$ and $R^{e8}$, independently of one another, are $C_1$-$C_4$-alkyl or $C_1$-$C_4$-alkoxy, and $R^{e2}$, $R^{e4}$, $R^{e5}$ and $R^{e7}$ are hydrogen. Preferably, $R^{e1}$, $R^{e3}$, $R^{e6}$ and $R^{e8}$, independently of one another, are selected from methyl, ethyl, isopropyl, tert-butyl and methoxy. In particular, $R^{e1}$, $R^{e3}$, $R^{e6}$ and $R^{e8}$ are all methyl.

In particular, in the compounds (VI.2), the group Y is a group of the formula (VII.b), in which $R^{II}$ and $R^V$ in each case both are methyl, ethyl, isopropyl or tert-butyl, and $R^I$, $R^{III}$, $R^{IV}$ and $R^{VI}$ are all hydrogen.

Preferably, in the compounds (VI.2), the group Y is selected from 3,3',5,5'-tetramethyl-1,1'-biphenyl-2,2'-diyl, 3,3',5,5'-tetraethyl-1,1'-biphenyl-2,2'-diyl, 3,3',5,5'-tetra-n-propyl-1,1'-biphenyl-2,2'-diyl, 3,3'-dimethyl-5,5'-dichloro-1,1'-biphenyl-2,2'-diyl, 3,3'-diethyl-5,5'-dibromo-1,1'-biphenyl-2,2'-diyl, 3,3'-dimethyl-5,5'-diiodo-1,1'-biphenyl-2,2'-diyl, 3,3'-dimethyl-5,5'-diethyl-1,1'-biphenyl-2,2'-diyl, 3,3'-dimethyl-5,5'-di-n-propyl-1,1'-biphenyl-2,2'-diyl, 3,3',5,5'-tetraisopropyl-1,1'-biphenyl-2,2'-diyl, 3,3',5,5'-tetra-n-butyl-1,1'-biphenyl-2,2'-diyl, 3,3',5,5'-tetraisobutyl-1,1'-biphenyl-2,2'-diyl, 3,3',5,5'-tetra-sec-butyl-1,1'-biphenyl-2,2'-diyl, 3,3',5,5-tetra-tert-butyl-1,1'-biphenyl-2,2'-diyl, 3,3'-di-tert-butyl-5,5'-di-namyl-1,1'-biphenyl-2,2'-diyl, 3,3',5,5'-tetrakis(1,1-dimethylpropyl)-1,1'-biphenyl-2,2'-diyl, 3,3'-di-tert-butyl-5,5'-bis(1,1-dimethylpropyl)-1,1'-biphenyl-2,2'-diyl, 3,3'-di-tert-butyl-5,5'-di-n-hexyl-1,1'-biphenyl-2,2'-diyl, 3,3'-di-tert-butyl-5,5'-di-2-hexyl-1,1'-biphenyl-2,2'-diyl, 3,3'-di-tert-butyl-5,5'-di-3-hexyl-1,1'-biphenyl-2,2'-diyl, 3,3'-di-tert-butyl-5,5'-di-n-heptyl-1,1'-biphenyl-2,2'-diyl, 3,3'-di-tert-butyl-5,5'-di-2-heptyl-1,1'-biphenyl-2,2'-diyl, 3,3'-di-tert-butyl-5,5'-di-3-heptyl-1,1'-biphenyl-2,2'-diyl, 3,3'-di-tert-butyl-5,5'-di-4-heptyl-1,1'-biphenyl-2,2'-diyl, 3,3'-di-tert-butyl-5,5'-di-n-octyl-1,1'-biphenyl-2,2'-diyl, 3,3'-Di-tert-butyl-5,5'-di-2-octyl-1,1'-biphenyl-2,2'-diyl, 5,5'-di-3-octyl-1,1'-biphenyl-2,2'-diyl, 3,3'-di-tert-butyl-5,5'-di-4-octyl-1,1'-biphenyl-2,2'-diyl, 3,3'-di-tert-butyl-5,5-bis(1,1,3,3-tetramethylbutyl)-1,1'-biphenyl-2,2'-diyl, 3,3',5,5'-tetrakis(1,1,3,3-tetramethylbutyl)-1,1'-biphenyl-2,2'-diyl, 3,3'-di-tert-butyl-5,5',6,6'-tetramethyl-1,1'-biphenyl-2,2'-diyl, 3,3'-di-tert-butyl-5,5-diphenyl-1,1'-biphenyl-2,2'-diyl, 3,3'-di-tert-butyl-5,5'-bis(2,4,6-trimethylphenyl)-1,1'-biphenyl-2,2'-diyl, 3,3'-di-tert-butyl-5,5'-dimethoxy-1,1'-biphenyl-2,2'-diyl, 3,3'-di-tert-butyl-5,5'-diethoxy-1,1'-biphenyl-2,2'-diyl, 3,3'-di-tert-butyl-5,5'-di-n-propoxy-1,1'-biphenyl-2,2'-diyl, 3,3'-di-tert-butyl-5,5'-diisopropoxy-1,1'-biphenyl-2,2'-diyl, 3,3'-di-tert-butyl-5,5-di-n-butoxy-1,1'-biphenyl-2,2'-diyl, 3,3'-di-tert-butyl-5,5'-di-sec-butoxy-1,1'-biphenyl-2,2'-diyl, 3,3'-di-tert-butyl-5,5'-diisobutoxy-1,1'-biphenyl-2,2'-diyl, 3,3'-di-tert-butyl-5,5'-di-tert-butoxy-1,1'-biphenyl-2,2'-diyl and 1,1'-binaphthalinyl-2,2'-diyl.

Particularly preferably, the group Y is 3,3',5,5-tetramethyl-1,1'-biphenyl-2,2'-diyl.

Particularly preferably, the hydroformylation catalyst used comprises at least one phosphorus chelate compound as ligand which is selected from among the compounds:

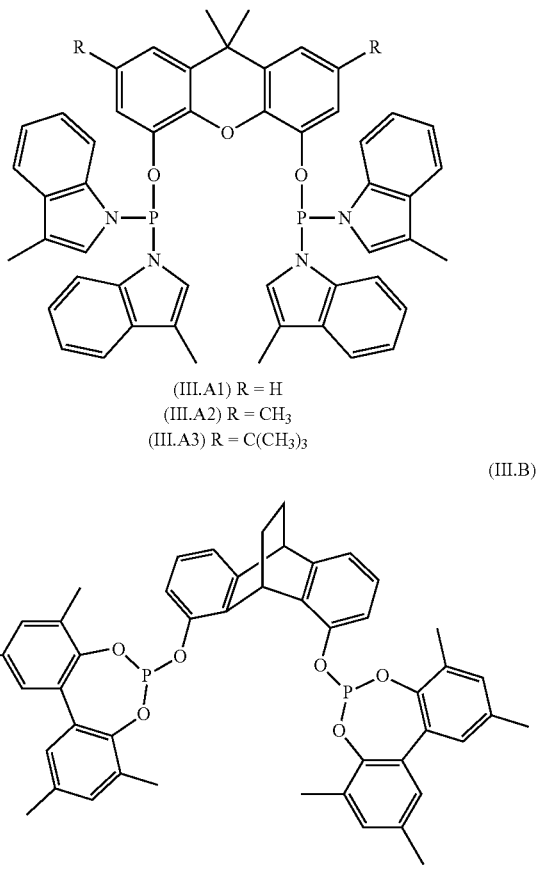

(III.A1) R = H
(III.A2) R = CH$_3$
(III.A3) R = C(CH$_3$)$_3$ (III.B)

Particularly preferably, in the process according to the invention, a hydroformylation catalyst is used which comprises [5-bis(3-methylindol-1-yl)phosphanyloxy-2,7-ditert-butyl-9,9-dimethyl-xanthen-4-yl]oxy-bis(3-methylindol-1-yl)phosphane (tBuSkatOX) as ligand.

Furthermore, in the process according to the invention, particular preference is given to using a hydroformylation catalyst which comprises the compound (III.B) (tMe-Rucaphosphite) as ligand.

tBuSkatOX and tMe-Rucaphosphite permit the hydroformylation of compounds of the general formula (II) and specifically of β-farnesene with high conversions, high selectivities as regards the hydroformylation of the vinyl group and high yields of the compound (I).

In addition to the phosphorus chelate compound used as ligand described above, the hydroformylation catalysts used according to the invention can also have, as ligands, at least one further ligand which is preferably selected from halides, amines, carboxylates, acetylacetonate, aryl- or alkylsulfonates, hydride, CO, olefins, dienes, cycloolefins, nitriles, N-containing heterocycles, aromatics and heteroaromatics, ethers, PF$_3$, phospholes, phosphabenzenes, and monodentate phosphine, phosphinite, phosphorite, phosphoramidite and phosphite ligands. Particularly suitable further ligands are hydride, carbonyl and triphenylphosphine. The transition metal complex catalyst can comprise two or more of the different ligands specified. Particularly preferably, the transition metal complex catalyst comprises a phosphorus chelate ligand, hydride and carbonyl or a phosphorus chelate ligand and hydride or a phosphorus chelate ligand and carbonyl.

The amount of metal components in the catalyst, preferably rhodium, is generally 0.1 to 5000 ppm by weight, in each case based on the total liquid reaction mixture.

The quantitative molar ratio of phosphorus-containing ligand to metal is generally in a range from about 1:1 to 1000:1, preferably in a range from 1:1 to 500:1.

The homogenous catalysts can be used either directly in their active form, or else be generated starting from transition metal sources with the addition of the corresponding ligands, specifically the aforementioned polydentate phosphorus chelate compounds, only under the reaction conditions. Preference is given to a process wherein the hydroformylation catalyst is produced in situ, with at least one of the ligands, a compound or a complex of the metal and optionally an activation agent being reacted in an inert solvent under the hydroformylation conditions.

Suitable transition metal sources are quite generally transition metals, transition metal compounds and transition metal complexes from which, in the reaction zone under the hydroformylation conditions, the hydroformylation catalyst is formed in situ.

Rhodium compounds or complexes suitable as transition metal source are e.g. rhodium(II) and rhodium(III) salts, such as rhodium(II) or rhodium(III) carboxylate, rhodium (II) and rhodium(III) acetate, etc. Also of suitability are rhodium complexes, such as rhodium biscarbonylacetylacetonate, acetylacetonatobisethylene rhodium(I), acetylacetonatocyclooctadienyl rhodium(I), acetylacetonatonorbornadienyl rhodium(I), acetylacetonatocarbonyltriphenylphosphine rhodium(I), etc.

The hydroformylation reaction can take place continuously, semicontinuously or discontinuously.

The hydroformylation takes place in a reaction zone which can comprise one or more identical or different reactors. In the simplest case, the reaction zone is formed by a single reactor. The reactors can in each case have identical or different mixing characteristics. The reactors can, if desired, be subdivided one or more times by means of internals. If two or more reactors form a zone, then these can be connected with one another as desired, e.g. in parallel or in series. Reactors which can be used are in principle all reactor types suitable for hydroformylation reactions, for example stirred reactors, bubble column reactors, as are described e.g. in U.S. Pat. No. 4,778,929, circulation reactors, as are e.g. the subject of EP-A 1 114 017, tubular reactors, where the individual reactors can have a series of different mixing characteristics, as described e.g. in EP-A 423 769; furthermore, compartmented reactors can be used, as are e.g. the subject of EP-A 1 231 198 or of U.S. Pat. No. 5,728,893. Suitable reactors for the continuous reaction are moreover known to the person skilled in the art and are described e.g. in Ullmanns Encyclopedia of Industrial Chemistry, vol. 1, 3$^{rd}$ edition, 1951, p. 743 ff.

Suitable pressure-resistant reactors are likewise known to the person skilled in the art and are described e.g. in Ullmanns Encyclopedia of Industrial Chemistry, vol. 1, 3$^{rd}$ edition, 1951, p. 769 ff. In general, an autoclave is used for the process according to the invention which can, if desired, be provided with a stirring device and an internal lining.

The composition of the synthesis gas of carbon monoxide and hydrogen used in the process according to the invention can vary within wide ranges. The molar ratio of carbon monoxide and hydrogen is generally about 5:95 to 70:30, preferably about 40:60 to 60:40. Particular preference is given to using a molar ratio of carbon monoxide and hydrogen in the region of about 1:1.

The temperature during the hydroformylation reaction is generally in a range from about 20 to 180° C., preferably about 50 to 150° C., particularly preferably 60 to 100° C. The reaction is generally carried out at the partial pressure of the reaction gas at the selected reaction temperature. In general, the pressure is in a range from about 1 to 700 bar, preferably 1 to 100 bar, in particular 5 to 60 bar. The reaction pressure can be varied depending on the activity of the hydroformylation catalyst according to the invention used. In general, the catalysts according to the invention based on phosphorus-containing compounds permit a conversion within a range of low pressures, such as for example in the range from 1 to 100 bar.

The hydroformylation can be carried out in a suitable solvent inert under the respective reaction conditions. Suitable solvents are e.g. the aldehydes formed during the hydroformylation and higher-boiling reaction components, e.g. the products of the aldol condensation. Also of suitability are aromatics, such as toluene and xylenes, hydrocarbons or mixtures of hydrocarbons, esters of aliphatic carboxylic acids with alkanols, for example Texanol®, and esters of aromatic carboxylic acids, e.g. $C_8$-$C_{13}$-dialkyl phthalates.

The hydroformylation catalysts according to the invention can be separated off from the discharge of the hydroformylation reaction by customary processes known to the person skilled in the art and can generally be reused for the hydroformylation.

The catalysts according to the invention advantageously exhibit a high activity, meaning that in general the corresponding aldehydes are obtained in good yields. The hydroformylation activity of the catalysts according to the invention is surprisingly generally higher than the isomerization activity as regards the double bonds which are not converted by hydroformylation.

The resulting reaction mixture can be subjected to a work-up by customary processes known to the person skilled in the art. For this, the reaction mixture obtained during the hydroformylation can be subjected to at least one work-up step to separate off at least one of the following components:
hydroformylation catalyst,
unreacted compounds of the formula (I),
reaction products different from the compounds of the formula (II.1),
solvents.

Hydrogenation (Step b)

In step b) of the process according to the invention, at least one aldehyde of the general formula (I) is subjected to a hydrogenation to give at least one compound of the general formula (III) $R^1$—C(=$CH_2$)—($CH_2$)$_2$—$CH_2$—OH. In a specific embodiment, (7E)-8,12-dimethyl-4-methylenetrideca-7,11-dienal (I.1) is subjected to a hydrogenation to give a compound of the formula (III.1). In the course of the preparation according to the invention of (−)-ambrox, this reaction step is referred to as step b1). Unless stated otherwise hereinbelow, the statements relating to step b) apply analogously to step b1).

The catalysts used according to the invention for the hydrogenation permit a good selectivity as regards the hydrogenation of the terminal aldehyde group to give the corresponding alcohol. The hydrogenation and the isomerization of the double bonds present in the compounds (I) or (I.1) can essentially be avoided.

Preferably, the hydrogenation in step b) or b1) is carried out in the presence of a transition metal catalyst soluble in the reaction mixture.

Preferred transition metal compounds are those of metals of subgroup VIII of the Periodic Table of the Elements, in particular Ru, Rh, Pd, Ir and Pt. Particular preference is given to Ru.

Of suitability are, for example, catalysts and catalyst precursors from which, under the hydrogenation conditions, catalytically active species of the general formula [$H_g Me_d (CO)_e G_f$] are formed, in which Me is a metal of subgroup VIII, G is a bi- or polydentate phosphorus-, arsenic- or antimony-containing ligand and d, e, f, g are integers dependent on the valency and type of metal and also on the covalence of the ligand G. Preferably, e and f, independently of one another, stand at least for a value of 1, such as e.g. 1, 2 or 3. The sum of e and f is preferably a value from 2 to 5. Suitable ligands G are selected from bi- and polydentate phosphine, phosphinite, phosphonite, phosphoramidite and phosphite ligands. Suitable catalysts can additionally have at least one further ligand which is preferably selected from triarylphosphines, triaryl-phosphites, triarylphosphinites, triarylphosphonites, $PF_3$, phospholes, phosphabenzenes, trialkylphosphines, phosphametallocenes, halides, amines, carboxylates, acetylacetonate, aryl- or alkylsulfonates, olefins, dienes, cycloolefins, ethers, nitriles, nonaromatic N-containing heterocycles, aromatics and heteroaromatics. A particularly preferred further ligand is triphenylphosphine (TPP).

In a specific embodiment, a catalyst is used for the hydrogenation which has at least one compound of the general formula (X)

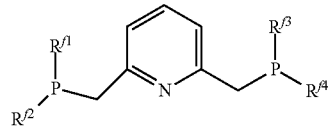

as ligand, in which
$R^{f1}$, $R^{f2}$, $R^{f3}$ and $R^{f4}$ independently of one another, are selected from $C_1$-$C_6$-alkyl.

Preferably, $R^{f1}$, $R^{f2}$, $R^{f3}$ and $R^{f4}$ have the same meaning.

A preferred ligand is di-tert-butyl-[[6-(di-tert-butylphosphanylmethyl)-2-pyridyl]-methyl]phosphane:

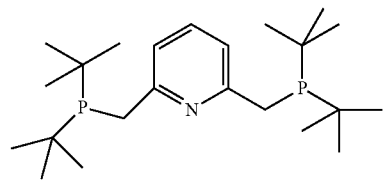 [SMILES: CC(C)(C)P(Cc1cccc(CP(C(C)(C)C)C(C)(C)C)n1)C(C)(C)C]

The hydrogenation catalysts can be produced in situ, in the reactor used for the hydrogenation reaction. If desired, the catalysts used according to the invention in step b) or b1) can also be produced separately and be isolated by customary processes. For the in situ production of the catalysts, a compound or a complex of a metal of subgroup VIII, if desired one or more ligands and optionally an activation agent can be reacted in an inert solvent under the hydrogenation conditions.

Suitable compounds of the specified transition metals are in particular those which are soluble in the selected reaction medium, such as, for example, salts or complex compounds with suitable ligands, such as e,g. carbonyl, acetylacetonate, hydroxy, cyclooctadiene, norbornadiene, cyclooctene, methoxy, acetyl or other aliphatic or aromatic carboxylates. Transition metal compounds preferred in the context of the process according to the invention are Ru(II), Ru(III), Ru(IV), Ru(0), Rh(I), Rh(III), Rh(0), Ir(I), Ir(III), Ir(IV), Ir(0) compounds, Pd(II), Pd(IV), Pd(0), Pt(II), Pt(IV) and Pt(0) compounds.

Suitable ruthenium salts are, for example, ruthenium(III) chloride, ruthenium(IV) oxide, ruthenium(VI) oxide or ruthenium(VIII) oxide, alkali metal salts of the ruthenium oxy acids, such as $K_2RuO_4$ or $KRuO_4$, or complex compounds of ruthenium. These include the metal carbonyls, such as trisruthenium dodecacarbonyl or hexaruthenium octadecacarbonyl, or mixed forms in which CO are partially replaced by ligands of the formula $PR_3$, such as $Ru(CO)_3(TPP)_2$.

Preference is given to those transition metal compounds which already have at least one CO ligand. In addition, it is also possible to use transition metal compounds which have no CO ligands as starting compound for producing the catalysts to be used according to the invention. These can then be converted to the desired catalysts in a preformation with CO and/or under the hydrogenation conditions with the addition of carbon monoxide.

In particular, the hydrogenation in step b) or b1) takes place in the presence of $HRuCl(CO)(TPP)_3$ as hydrogenation catalyst.

The specified transition metal compounds are usually used in an amount of from about 0.01 to about 1 mol %, preferably from about 0.05 to about 0.5 mol %, in particular from about 0.02 to about 0.2 mol % (based on the transition metal atoms present) relative to the amount of substrate to be hydrogenated.

During conversions carried out under continuous conditions, the ratio of amount of transition metal compound used as precursor of the homogenous catalyst according to the invention to the amount of substrate to be hydrogenated is advantageously selected in such a way that the catalyst concentration in the reaction mixture is in the range from about 10 ppm to 100 000 ppm, particularly preferably 50 ppm to 50 000 ppm, in particular in the range from 100 ppm to 10 000 ppm.

The hydrogenation in step b) or b1) advantageously takes place at a pressure of from about 1 to about 300 bar, preferably from about 2 to about 200 bar, in particular at about 3 to about 100 bar, specifically from about 5 to about 50 bar.

The hydrogenation in step b) or b1) advantageously takes place at a temperature of about 0 to 320° C., preferably from 20 to 300° C., in particular from 50 to 280° C.

Suitable solvents are, for example, ether, tetrahydrofuran, toluene, chlorobenzene, octadecanol, biphenyl ether, texanol, marlotherm, and oxo oil 9N (hydroformylation products from isomeric octenes, BASF SE).

Usually, the hydrogenation is concluded after about 1 to about 150 h, often after about 2 to about 48 h.

The resulting reaction product can be removed from the reaction mixture by processes known per se to the person skilled in the art, such as e.g. by distillation, and the remaining catalyst can be utilized in the course of further conversions, optionally after repeated preformation.

The hydrogenation in step b) or b1) can be operated discontinuously or continuously and is particularly suitable for reactions on an industrial scale.

Isomerization (Step c)

In step c) of the process according to the invention, at least one alcohol of the general formula (III) is subjected to an isomerization to give at least one compound of the general formula (IV):

In a specific embodiment, (7E)-8,12-dimethyl-4-methylenetrideca-7,11-dienol (III.1) is subjected to an isomerization to give (3E,7E)-homofarnesol (IV.1). In the course of the preparation according to the invention of (−)-ambrox, this reaction step is referred to as step c1). Unless stated otherwise hereinbelow, the statements relating to step c) apply analogously to step c1).

A suitable process for the isomerization of alcohol of the general formula (III) to give isomers of the general formula (IV) is described in WO 2014/114615, to which reference is made here in its entirety.

Preferably, the isomerization in step c) or c1) takes place in the presence of a catalyst of the formula

[Ru(dienyl)$_2$H]A in which dienyl is a $C_5$-$C_{22}$ hydrocarbon group which has a carbon-carbon double bond and a group C=C—C—, and A is a weakly coordinating or noncoordinating anion.

In a preferred embodiment of the invention, the group A stands for a weakly or noncoordinating monoanion. Preferably, A is $NO_3^-$, $HSO_4^-$, $BF_4^-$, $PF_6^-$, $SbF_6^-$, $AsF_6^-$, $F^-$ or $R^XSO_3^-$, where $R^X$ is a fluorine atom or a $C_{1-8}$-alkyl group or a $C_{1-8}$-fluoroalkyl group. Fluoroalkyl group here refers to a partially or completely fluorinated alkyl group, such as $CF_3$.

In a preferred embodiment of the invention, the group A is a monoanion.

In particular, the group A is $BF_4^-$, $PF_6^-$, $SbF_6^-$, $AsF_6^-$, $F^-$ or $R^XSO_3^-$ where $R^X$ is a fluorine atom or $CH_3$, $CF_3$, phenyl or p-tolyl.

In a specific embodiment, the group A is $BF_4^-$.

In a preferred embodiment, "dienyl" is a deprotonated diene, where diene is a $C_5$-$C_{22}$ hydrocarbon group which has two carbon-carbon double bonds and is not aromatic. Therefore, "dienyl" comprises a carbon-carbon double bond and a group C=C—C—.

In a preferred embodiment of the invention, "dienyl" and the starting diene is a linear, branched or cyclic group.

Preferably, "dienyl" is a deprotonated diene, where the diene is a $C_5$-$C_{12}$ hydrocarbon group.

Suitable "dienyls" are cyclooctadienyls, such as 2,4-dimethylpentadienyl, 2,3,4-trimethylpenta-1,3-dienyl, 2,7-dimethyloctadienyl or cycloheptadienyl. Correspondingly, the diene from which the dienyl radical is derived is selected from 1,3-, 1,4- or 1,5-cyclooctadiene, norbornadiene, 2,4-dimethyl-1,3-pentadiene, 2,3,4-trimethylpenta-1,3-diene, 2,7-dimethyl-2,6-octadiene or cyclohepta-1,4-diene.

In a preferred embodiment, the complex [Ru(dienyl)$_2$H]A is selected from [Ru(cyclooctadienyl)$_2$H]A, [Ru(cycloheptadienyl)₂H]A, [Ru(2,3,4-trimethylpenta-1,3-dienyl)₂H]A or [Ru(2,4-dimethylpentadienyl)₂H]A.

Suitable complexes [Ru(dienyl)₂H]A are known or can be prepared by known processes, as are described e.g. in FR 2887253, EP 1283843, in Salzer et al., OM 2000, (19), 5471, in Cox and Roulet, Chem. Commun., 1988, 951 or in F. Bouachir et al., Nouv. J. Chim., 1987, 11, 527.

The use amount of the complex is in principle not critical. It can be used for example in an amount of from 0.01 to 15 mol %, preferably from 0.2 to 2 mol %, based on the compound to be isomerized.

The isomerization in step c) or c1) can be carried out in the presence of a gas inert under the reaction conditions. Suitable inert gases are nitrogen, argon and mixtures thereof.

The reaction can take place in the presence or absence of an added solvent. Suitable solvents are aromatic hydrocarbons, such as benzene, toluene or xylene, $C_3$-$C_9$ esters, such as AcOEt, chlorinated solvents, such as methylene chloride, chloroform or dichloroethane, $C_2$-$C_9$ ethers, such as tetrahydrofuran, methyltetrahydrofuran, dimethoxyethanes, diethyl ether, $C_2$-$C_9$ alcohols, such as methanol, ethanol, and mixtures of the aforementioned solvents.

Preferably, the temperature during the isomerization in step b) or b1) is in a range from 10° C. to 95° C., more preferably from 20° C. to 60° C.

Cyclization (Step d1)

According to the specific embodiment of the process according to the invention for the preparation of (−)-ambrox, in the concluding step d1), (3E,7E)-homofarnesol (IV.1) is subjected to a cyclization to give (−)-ambrox (V).

As already mentioned at the start, the cyclization of (3E,7E)-homofarnesol to ambrox is known, with both enzymatic and chemical cyclizations being described. In this connection, reference is made to the disclosure of the following documents:

P. F. Vlad et al. *Khimiya Geterotsiklicheskikh Soedinenii, Engl. Transl.* 1991, 746 describe cyclization reactions using a super acid (fluorosulfonic acid in 2-nitropropane), A further suitable process comprises the enantioselective polyene cyclization of homofarnesyl triethylsilyl ether in the presence of O-(o-fluorobenzyl)-binol and $SnCl_4$, as described by H. Yamamoto et al. J. Am. Chem. Soc. 2002, 3647.

Preference is given to the biocatalytic cyclization as described in WO 2010/139719. According to this, the cyclization in step d1) takes place in the presence of a polypeptide with the activity of a homofarnesol-ambrox-cyclase as enzyme.

To prepare (−)-ambrox according to this variant, homofarnesol is brought into contact with the homofarnesol-ambroxan-cyclase and/or incubated and then the formed ambrox is isolated.

In one embodiment of step d1), homofarnesol is brought into contact with the homofarnesol-ambroxan-cyclase in a medium and/or incubated such that a conversion of homofarnesol to ambrox takes place in the presence of the cyclase. Preferably, the medium is an aqueous reaction medium. The aqueous reaction media are preferably buffered solutions which generally have a pH of preferably 5 to 8. As buffer, it is possible to use a citrate, phosphate, TRIS (tris(hydroxymethyl)aminomethane) or MES (2-(N-morpholino)ethanesulfonic acid) buffer. Furthermore, the reaction medium can also comprise further additives, such as e.g. detergents (for example taurodeoxycholate).

The homofarnesol is preferably used in a concentration of from 5 to 100 mM, particularly preferably from 15 to 25 mM, in the enzymatic reaction. This can be carried out continuously or discontinuously.

The enzymatic cyclization in step d1) expediently takes place at a reaction temperature below the deactivation temperature of the cyclase used. Preferably, the reaction temperature in step d1) is in a range from −10 to 100° C., particularly preferably from 0 to 80° C., in particular from 15 to 60° C. and specifically from 20 to 40° C.

The reaction product ambrox can be extracted with organic solvents and optionally be distilled for purification. Suitable solvents are specified below.

Besides single-phase aqueous systems, it is also possible to use two-phase systems. In this variant, it is possible to enrich the formed ambrox in the nonaqueous phase in order to isolate it. The second phase is preferably selected here from ionic liquids and organic non-water-miscible solvents. After the reaction, ambrox in the organic phase can be separated off easily from the aqueous phase which comprises the biocatalyst. Non-aqueous reaction media are understood as meaning reaction media which comprise less than 1% by weight, preferably less than 0.5% by weight, of water, based on the total weight of the liquid reaction medium. In particular, the conversion can be carried out in an organic solvent. Suitable organic solvents are, for example, aliphatic hydrocarbons, preferably with 5 to 8 carbon atoms, such as pentane, cyclopentane, hexane, cyclohexane, heptane, octane or cyclooctane, halogenated aliphatic hydrocarbons, preferably with one or two carbon atoms, such as dichloromethane, chloroform, tetrachloromethane, dichloroethane or tetrachloroethane, aromatic hydrocarbons, such as benzene, toluene, the xylenes, chlorobenzene or dichloro-benzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate, or ketones such as methyl isobutyl ketone or dioxane or mixtures thereof. Particular preference is given to using the aforementioned heptane, methyl tert-butyl ether, diisopropyl ether, tetrahydrofuran, ethyl acetate.

Suitable enzymes are described in WO 2010/139719, to which reference is made here in its entirety. According to this, the enzyme is a polypeptide which is coded by a nucleic acid molecule comprising at least one nucleic acid molecule selected from:

a) nucleic acid molecule which codes for a polypeptide comprising SEQ ID NO 2, 5, 6, 7, 8, 9, 10 or 11; b) nucleic acid molecule which comprises at least one polynucleotide of the sequence shown in SEQ ID NO 1; c) nucleic acid molecule which codes for a polypeptide whose sequence has an identity of at least 46% to the sequences SEQ ID NO 2, 5, 6, 7, 8, 9, 10 or 11; d) nucleic acid molecule according to (a) to (c) which represents a functionally equivalent polypeptide or a fragment of the sequence according to SEQ ID NO 2, 5, 6, 7, 8, 9, 10 or 11; e) nucleic acid molecule coding for a functionally equivalent polypeptide with the activity of a homofarnesol-ambroxan-cyclase which is obtained by amplifying a nucleic acid molecule from a cDNA bank or from genomic DNA by means of the primer according to sequence No. 3 and 4, or chemically synthesizing the nucleic acid molecule by de novo synthesis; f) nucleic acid molecule coding for a functionally equivalent polypeptide with the activity of a homo-farnesol-ambroxan-cyclase which hybridizes under stringent conditions with a nucleic acid molecule according to (a) to (c); g) nucleic acid molecule coding for a functionally equivalent polypeptide with the activity of a homofarnesol-ambroxan-cyclase which can be isolated from a DNA bank using a nucleic acid molecule according to (a) to (c) or part fragments thereof of at least 15 nt, preferably 20 nt, 30 nt, 50 nt, 100 nt, 200 nt or 500 nt as probe under stringent hybridization conditions; and h) nucleic acid molecule coding for a functionally equivalent polypeptide with the activity of a homofarnesol-ambroxan-cyclase, where the sequence of the polypeptide has an identity of at least 46% to the sequences SEQ ID NO 2, 5, 6, 7, 8, 9, 10 or 11; i) nucleic acid molecule coding for a functionally equivalent polypeptide with the activity of a homofarnesol-ambroxan-cyclase, where the polypeptide is coded by a nucleic acid molecule selected from the group of those described in a) to h) and has been isolated, or can be isolated, by means of a monoclonal antibody; j) nucleic acid molecule coding for a functionally equivalent polypeptide with the activity of a homofarnesol-ambroxan-cyclase, where the polypeptide has an analogous or similar binding site to a polypeptide coded by a nucleic acid molecule selected from the group of those described in a) to h)).

Despite a large number of already present aroma chemicals (fragrances and flavors) and processes for their production, there is a constant need for new components in order to be able to satisfy the multitude of properties desired for extremely diverse fields of use, and also for simple synthesis routes in order to make these accessible. The process according to the invention permits the effective preparation of compounds of the general formula (I) which can serve as interesting synthesis building blocks in the provision of new and already known aroma chemicals, such as (−)-ambrox. Following hydrogenation of the aldehyde function, alcohols can be obtained which, for their part, may be interesting synthesis building blocks and are suitable for use as surfactant alcohols.

The invention is described in more detail by the working examples below.

EXAMPLES

Example 1

5.1 mg of rhodium biscarbonylacetylacetonate and 92.3 mg of $^{tBu}$SkatOX (ligand-metal ratio=5:1) were dissolved in 10 g of THF and placed into a 100 ml autoclave flushed with $CO/H_2$ (1:1) using a syringe. Then, at 10 bar $CO/H_2$ (1:1) and 70° C., preformation was carried out for 30 min. The system was then decompressed and 10 g of trans-ß-farnesene were added using a syringe. The hydroformylation was carried out at 70° C. and 40 bar $CO/H_2$ (1:1). Analysis of the reaction discharge after a reaction time of 48 hours revealed a conversion of 92.5% with a selectivity to the target product (7E)-8,12-dimethyl-4-methylenetrideca-7,11-dienal of 70.4% and a yield of target product of 65.1%.

Example 2

5.1 mg of rhodium biscarbonylacetylacetonate and 92.3 mg of $^{tBu}$SkatOX (ligand-metal ratio=5:1) were dissolved in 10 g of THF and placed into a 100 ml autoclave flushed with $CO/H_2$ (1:1) using a syringe. Then, at 10 bar $CO/H_2$ (1:1) and 70° C., preformation was carried out for 30 min. The system was then decompressed and 10 g of trans-ß-farnesene were added using a syringe. The hydroformylation was carried out at 70° C. and 40 bar $CO/H_2$ (1:1). Analysis of the reaction discharge after a reaction time of 70 hours revealed a conversion of 99.3% with a selectivity to the target product (7E)-8,12-dimethyl-4-methylenetrideca-7,11-dienal of 68.6% and a yield of target product of 68.1%.

Example 3

5.1 mg of rhodium biscarbonylacetylacetonate and 44.4 mg of tMe-Rucaphosphite (ligand-metal ratio=3:1) were dissolved in 10 g of THF and placed into a 100 ml autoclave flushed with $CO/H_2$ (1:1) using a syringe. Then, at 10 bar $CO/H_2$ (1:1) and 70° C., preformation was carried out for 30 min. Then, the system was decompressed and 10 g of trans-ß-farnesene were added using a syringe. The hydroformylation was carried out at 90° C. and 40 bar $CO/H_2$ (1:1). Analysis of the reaction discharge after a reaction time of 48 hours revealed a conversion of 87.3% with a selectivity to the target product (7E)-8,12-dimethyl-4-methylenetrideca-7,11-dienal of 71.9% and a yield of target product of 62.7%.

Example 4

Hydrogenation of (7E)-8,12-Dimethyl-4-methylenetrideca-7,11-dienal (7E)-8,12-Dimethyl-4-methylenetrideca-7,11-dienal was used in an autoclave as solution in THF in the weight ratio 1:1 for the hydrogenation. Based on starting material, 0.25 mol % of [HRuCl(CO)(TPP)$_3$] and di-tert-butyl-[[6-(di-tert-butylphosphanylmethyl)-2-pyridyl]methyl]phosphane in the weight ratio chelate ligand:ruthenium of 1:1.3 was added. Then, hydrogen was injected into the autoclave, which was heated to 250° C., reaching a pressure of 12 bar. After a reaction time of 24 hours, it was left to cool, the autoclave was decompressed and the reaction discharge was analyzed by means of NMR spectroscopy. The yield of product alcohol was about 80%. Isomerization of the double bonds was not observed.

The invention claimed is:

1. A process for the preparation of compounds of the general formula (I) and of secondary products thereof,

(I)

comprising reacting at least one compound of the general formula (II)

(II)

in which
R$^1$ is in each case linear or branched $C_1$-$C_{24}$-alkyl or $C_2$-$C_{24}$-alkenyl having 1, 2, 3 or more than 3 C—C double bonds,
with carbon monoxide and hydrogen in the presence of a hydroformylation catalyst comprising a rhodium complex with at least one phosphorus chelate compound as ligand, the hydroformylation catalyst comprising at least one phosphorus chelate compound of the general formula (VI)

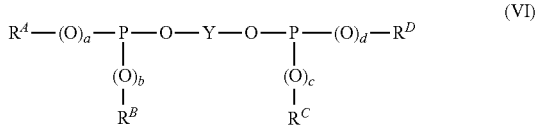

(VI)

in which
R$^A$, R$^B$, R$^C$ and R$^D$, independently of one another, are alkyl, cycloalkyl, heterocycloalkyl, aryl or hetaryl,
where the alkyl radicals R$^A$, R$^B$, R$^C$ and R$^D$ are unsubstituted or carry 1, 2, 3, 4 or 5 identical or different substituents which are selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, COOH, carboxylate, SO$_3$H, sulfonate, NE$^1$E$^2$, NE$^1$E$^2$E$^{3+}$X$^-$, halogen, nitro, formyl, acyl and cyano, in which E$^1$, E$^2$ and E$^3$ are in each case identical or different radicals selected from hydrogen, alkyl, cycloalkyl or aryl, and X$^-$ is an anion equivalent,
and where the cycloalkyl, heterocycloalkyl, aryl and hetaryl radicals RA, RB, RC and RD are in each case unsubstituted or carry 1, 2, 3, 4 or 5 identical or different substituents which are selected from alkyl and the substituents specified above for the alkyl radicals R$^A$, R$^B$, R$^C$ and R$^D$,
or
R$^A$ and R$^B$ and/or R$^C$ and R$^D$, together with the phosphorus atom and, if present, the oxygen atoms to which they are bonded, are a 5- to 8-membered heterocycle which is optionally additionally annelated once, twice or three times with cycloalkyl, heterocycloalkyl, aryl or hetaryl, where the heterocycle and, if present, the annelated groups are, independently of one another, unsubstituted or carry one, two, three or four identical or different substituents which are selected from alkyl, cycloalkyl, heterocycloalkyl, aryl, hetaryl, hydroxy, mercapto, polyalkylene oxide, polyalkyleneimine, alkoxy, halogen, COOH, carboxylate, SO$_3$H, sulfonate, NE$^4$E$^5$, NE$^4$E$^5$E$^{6+}$X$^-$, nitro, alkoxycarbonyl, formyl, acyl and cyano, in which E$^4$, E$^5$ and E$^6$ are in each case identical or different radicals, selected from hydrogen, alkyl, cycloalkyl and aryl, and X$^-$ is an anion equivalent,
a, b, c and d, independently of one another, are 0 or 1, and
Y is selected from groups of the formula VII.a or VII.b

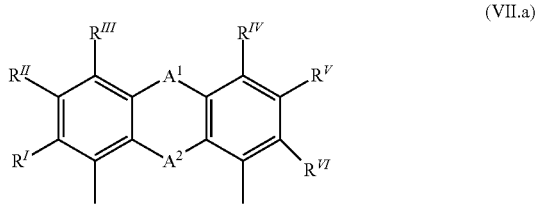

(VII.a)

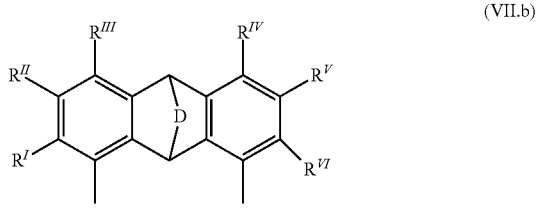

(VII.b)

in which
R$^I$, R$^{II}$, R$^{III}$, R$^{IV}$, R$^V$ and R$^{VI}$, independently of one another, are hydrogen, alkyl, cycloalkyl, heterocycloalkyl, aryl, hetaryl, hydroxy, mercapto, polyalkylene oxide, polyalkyleneimine, alkoxy, halogen, SO$_3$H, sulfonate, NE$^7$E$^8$, alkylene-NE$^7$E$^8$, trifluoromethyl, nitro, alkoxycarbonyl, carboxyl, formyl, acyl or cyano, in which E$^7$ and E$^8$ are in each case identical or different radicals selected from hydrogen, alkyl, cycloalkyl and aryl,
where two adjacent radicals R$^I$ to R$^{VI}$, together with the carbon atoms of the benzene ring to which they are bonded, can also be a condensed ring system having 1, 2 or 3 further rings,
A$^1$ and A$^2$, independently of one another, are O, S, SiR$^E$R$^F$, NR$^G$ or CR$^H$R$^K$, where R$^E$, R$^F$, R$^G$, R$^H$ and R$^K$, independently of one another, are hydrogen, alkyl, cycloalkyl, heterocycloalkyl, aryl or hetaryl, and
D is a divalent bridging group of the general formula

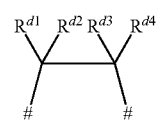

in which
# is in each case a binding site to the 9,10-dihydroanthracene backbone, and
R$^{d1}$, R$^{d2}$, R$^{d3}$ and R$^{d4}$, independently of one another, are hydrogen, alkyl, cycloalkyl, aryl, halogen, trifluoromethyl, carboxyl, carboxylate or cyano,
where R$^{d1}$ can also be, together with R$^{d3}$, the binding fraction of a double bond between the two carbon atoms to which R$^{d1}$ and R$^{d3}$ are bonded, and/or R$^{d2}$ and R$^{d4}$, together with the carbon atoms to which they are bonded, can also be a 4- to 8-membered carbo- or heterocycle, which is optionally additionally annelated once, twice or three times with cycloalkyl, heterocycloalkyl, aryl or hetaryl, where the carbo- or heterocycle and, if present, the annelated groups are, independently of one another, unsubstituted or in each case carry one, two, three or four identical or different substituents which are selected from alkyl, cycloalkyl, heterocycloalkyl, aryl, hetaryl, COOR$^{d5}$, COO$^-$M$^+$, SO$_3$R$^{d5}$, SO$_3$$^-$M$^+$, NE$^9$E$^{10}$, alkylene-NE$^9$E$^{10}$, NE$^9$E$^{10}$E$^{11+}$X$^-$, alkylene-NE$^9$E$^{10}$E$^{11+}$X$^-$, OR$^{d6}$, SR$^{d6}$, (CHR$^f$CH$_2$O)$_y$R$^{d6}$, (CH$_2$N(E$^9$))$_y$R$^{d6}$, (CH$_2$CH$_2$N(E$^9$))$_y$R$^{d6}$, halogen, trifluoromethyl, nitro, formyl, acyl or cyano, in which
R$^{d5}$, E$^9$, E$^{10}$ and E$^{11}$ are in each case identical or different radicals selected from hydrogen, alkyl, cycloalkyl or aryl,
R$^{d6}$ is hydrogen, methyl or ethyl,
M$^+$ is a cation equivalent,
X$^-$ is an anion equivalent, and
Y is an integer from 1 to 120,
wherein a reaction mixture is obtained which comprises at least 50.1% by weight, based on the total weight of the reaction mixture, of at least one compound of the general formula (I).

2. The process according to claim 1, further comprising hydrogenating the reaction mixture obtained in the hydroformylation step or a fraction thereof enriched in at least one compound of the general formula (I), wherein a reaction mixture is obtained which comprises at least one compound of the general formula (III)

(III)

[Structure: R¹ group with =CH₂ and chain ending in OH]

3. The process according to claim 2, which further comprises at least partially isomerizing the at least one compound of the general formula (III) to give a compound of the general formula (IV)

(IV)

[Structure: R¹ group with chain ending in OH]

4. The process according to claim 1, wherein the compounds of the formula (II) have only one vinyl group in the molecule.

5. The process according to claim 1, wherein the compound of the general formula (II) is selected from the group consisting of isoprene, β-myrcene and β-farnesene.

6. The process according to claim 1, wherein the reaction mixture obtained in the hydroformylation step comprises at least 55% by weight, based on the total weight of the reaction mixture, of at least one compound of the general formula (I).

7. The process according to claim 1, wherein the reaction mixture obtained in the hydroformylation step comprises at least 60% by weight, based on the total weight of the reaction mixture, of at least one compound of the general formula (I).

8. The process according to claim 1, wherein the reaction mixture obtained in the hydroformylation step comprises at least 65% by weight based on the total weight of the reaction mixture, of at least one compound of the general formula (I).

9. The process according to claim 1, wherein the compound of general formula (II) is β-farnesene and the reaction mixture obtained comprises at least 50.1% by weight, based on the total weight of the reaction mixture, of (7E)-8,12-dimethyl-4-methylenetrideca-7,11-dienal.

10. The process according to claim 1, wherein the reaction mixture obtained in the hydroformylation step is subjected to at least one work-up step to separate off at least one of the following components:
hydroformylation catalyst,
reaction products different from the compounds of the formula (I),
unreacted compounds of the formula (II), or
solvents.

11. The process according to claim 1, wherein the hydroformylation catalyst comprises at least one phosphorus chelate compound of the general formula (VI.1)

(VI.1)

$$R^A-P(R^B)-O-Y-O-P(R^C)-R^D$$

in which
Y has the meaning given above, and
the radicals $R^A$, $R^B$, $R^C$ and $R^D$, independently of one another, are selected from groups of the formula VIII.a to VIII.k (VIII.a) [N-methylpyrrole with Alk groups at 2,5]

(VIII.b) [N-methylpyrrole with Alk and COOAlk]

(VIII.c) [N-methylpyrrole with COOAlk at 2,5]

(VIII.d) [N-methylpyrrole with COOAlk at 3,4]

(VIII.e) [N-methylindole with $R^a$, $R^b$]

(VIII.f) [N-methylindole with $R^a$, $R^b$, Alk]

(VIII.g) [N-methylindole with $R^a$, $R^b$, Alk, Alk]

(VIII.h) [N-methylindole with $R^a$, $R^b$, C(=O)Alk]

(VIII.i) [N-methylindole with $R^a$, $R^b$, COOAlk]

-continued (VIII.k)

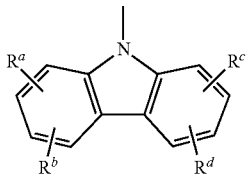

in which
Alk is a $C_1$-$C_4$-alkyl group and
$R^a$, $R^b$, $R^c$ and $R^d$, independently of one another, are hydrogen, $C_1$-$C_4$-alkyl, $C_1$-$C_4$-alkoxy, formyl, acyl, halogen, $C_1$-$C_4$-alkoxycarbonyl or carboxyl.

12. The process according to claim 1, where the hydroformylation catalyst comprises at least one phosphorus chelate compound of the general formula (VI.2)

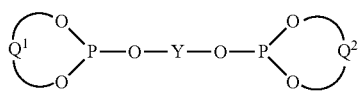
(VI.2)

in which
Y has the meaning given above, and
$Q^1$ and $Q^2$, independently of one another, are a divalent bridging group of the general formula (IX),

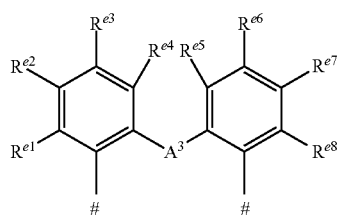
(IX)

in which
# is in each case a binding site to the phosphite group,
$R^{e1}$, $R^{e2}$, $R^{e3}$, $R^{e4}$, $R^{e5}$, $R^{e6}$, $R^{e7}$ and $R^{e8}$, independently of one another, are hydrogen, in each case unsubstituted or substituted alkyl, alkoxy, cycloalkyl, cycloalkoxy, heterocycloalkyl, heterocycloalkoxy, aryl, aryloxy, hetaryl, hetaryloxy,
halogen, hydroxy, mercapto, cyano, nitro, formyl, acyl, carboxy, carboxylates, alkylcarbonyloxy, carbamoyl, sulfo, sulfonate or $NE^{12}E^{13}$, in which $E^{12}$ and $E^{13}$ are in each case identical or different radicals selected from hydrogen, alkyl, cycloalkyl, heterocycloalkyl, aryl or hetaryl,
where two adjacent radicals $R^{e1}$ to $R^{e8}$, together with the carbon atoms of the benzene ring to which they are bonded, can also be a condensed ring system having 1, 2 or 3 further rings, and
$A^3$ is a single bond, O, S, $NR^{a31}$, $SiR^{a32}R^{a33}$ or $C_1$-$C_4$-alkylene which can have a double bond and/or an alkyl, cycloalkyl, heterocycloalkyl, aryl or hetaryl substituent, or can be interrupted by O, S, $NR^{a31}$ or $SiR^{a32}R^{a33}$, where $R^{a31}$, $R^{a32}$ and $R^{a33}$, independently of one another, are hydrogen, alkyl, cycloalkyl, heterocycloalkyl, aryl or hetaryl.

13. The process according to claim 1, wherein the hydroformylation catalyst comprises at least one phosphorus chelate compound as ligand which is selected from the compounds:

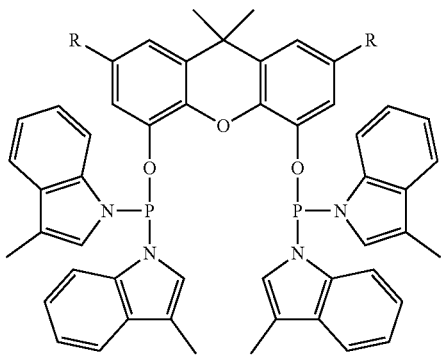

(VI.A1) R = H
(VI.A2) R = $CH_3$
(VI.A3) R = $C(CH_3)_3$

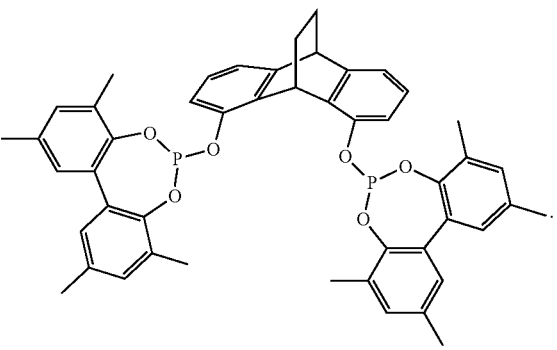
(VI.B)

14. A process for the preparation of (−)-ambrox ((3aR, 5aS,9aS,9bR)-3a,6,6,9a-tetramethyldodecahydronaphtho[2, 1-b]furan) (V)

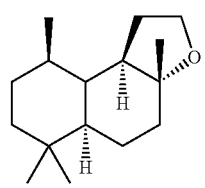
(V)

comprising
a1) reacting (6E)-7,11-dimethyl-3-methylidenedodeca-1, 6,10-triene (II.1)

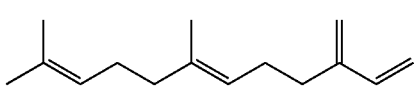
(II.1)

with carbon monoxide and hydrogen in the presence of a hydroformylation catalyst comprising a rhodium complex with at least one phosphorus chelate compound as ligand, wherein a reaction mixture is obtained which comprises at least 50.1% by weight, based on the total weight of the reaction mixture, of (7E)-8,12-dimethyl-4-methylenetrideca-7,11-dienal (I.1)

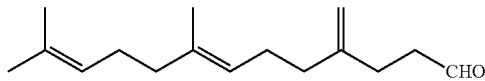
(I.1)

b1) hydrogenating the reaction mixture obtained in step a1) or a fraction thereof enriched in at least one compound of the general formula (I.1), wherein a reaction mixture is obtained which comprises the compound (111.1)

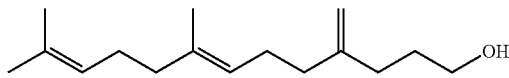
(III.1)

c1) at least partially isomerizing the compound (111.1), giving (3E,7E)-homofarnesol (IV.1)

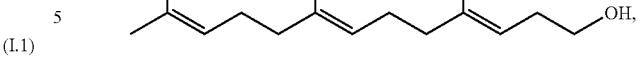
(IV.1)

and d1) cyclizing the (3E,7E)-homofarnesol (IV.1) to give (−)-ambrox (V).

15. The process according to claim 14 wherein the hydrogenation in step b1) takes place in the presence of a homogenous ruthenium catalyst.

16. The process according to claim 14, wherein the isomerization in step c1) takes place in the presence of a catalyst of the formula

[Ru(dienyl)$_2$H]A in which dienyl is a $C_5$-$C_{22}$-hydrocarbon group which has a carbon-carbon double bond and a group C=C—C$^-$, and A is a weakly coordinating or noncoordinating anion.

17. The process according to claim 14, wherein the cyclization in step d1) takes place in the presence of a polypeptide with the activity of a homofarnesol-ambroxcyclase as enzyme.

* * * * *